US008650798B1

(12) United States Patent
Armstrong et al.

(10) Patent No.: US 8,650,798 B1
(45) Date of Patent: Feb. 18, 2014

(54) METHOD OF REMOVING ALGAE ADHERED INSIDE A BIOREACTOR THROUGH COMBINED BACKWASHING AND LOWERING OF PH LEVEL

(75) Inventors: Richard L. Armstrong, Murrells Inlet, SC (US); Timothy G. Tompkins, Pawleys Island, SC (US)

(73) Assignee: Renewed World Energies, Georgetown, SC (US)

( * ) Notice: Subject to any disclaimer, the term of this patent is extended or adjusted under 35 U.S.C. 154(b) by 426 days.

(21) Appl. No.: 12/896,588

(22) Filed: Oct. 1, 2010

Related U.S. Application Data

(60) Provisional application No. 61/248,398, filed on Oct. 2, 2009.

(51) Int. Cl.
*A01G 7/00* (2006.01)
*A01H 13/00* (2006.01)

(52) U.S. Cl.
USPC ............................................................ 47/1.4

(58) Field of Classification Search
USPC .......................................... 47/1.4, 59 R, 62 A
See application file for complete search history.

(56) References Cited

U.S. PATENT DOCUMENTS

| 3,955,318 | A | * | 5/1976 | Hulls | ............................... | 47/1.4 |
| 5,242,827 | A | * | 9/1993 | Chaumont et al. | ......... | 435/292.1 |
| 5,476,787 | A | * | 12/1995 | Yokoyama et al. | ........ | 435/262.5 |
| 5,541,056 | A | * | 7/1996 | Huntley et al. | .................... | 435/3 |
| 5,882,849 | A | * | 3/1999 | Leonard et al. | .................... | 435/3 |
| 2002/0034817 | A1 | * | 3/2002 | Henry et al. | ............... | 435/257.1 |
| 2005/0064577 | A1 | * | 3/2005 | Berzin | .......................... | 435/266 |
| 2005/0239182 | A1 | * | 10/2005 | Berzin | .......................... | 435/166 |
| 2005/0260553 | A1 | * | 11/2005 | Berzin | ............................. | 435/3 |
| 2007/0092962 | A1 | * | 4/2007 | Sheppard | ....................... | 435/266 |
| 2007/0289206 | A1 | * | 12/2007 | Kertz | ................................ | 47/1.4 |
| 2008/0009055 | A1 | * | 1/2008 | Lewnard | ........................ | 435/262 |
| 2008/0118964 | A1 | * | 5/2008 | Huntley et al. | ............... | 435/166 |
| 2008/0178739 | A1 | * | 7/2008 | Lewnard et al. | ................. | 95/186 |
| 2009/0011492 | A1 | * | 1/2009 | Berzin | ....................... | 435/257.1 |
| 2009/0029445 | A1 | * | 1/2009 | Eckelberry et al. | ......... | 435/257.1 |
| 2009/0081743 | A1 | * | 3/2009 | Hazelbeck et al. | ........... | 435/157 |
| 2011/0062080 | A1 | * | 3/2011 | Galgon et al. | ................ | 210/631 |

* cited by examiner

Primary Examiner — Monica Williams
Assistant Examiner — Michael A Fabula
(74) Attorney, Agent, or Firm — James G. Passé; Passé Intellectual Property, LLC

(57) ABSTRACT

An algae bioreactor having a system and method for the efficient cultivation of algae in systems using in part or in full bioreactor chambers and other units wherein algae are grown in the presence of light and are then harvested for various uses including, but not limited to, for producing specific molecules, including recombinant molecules and other molecules produced from algae especially adapted to produce such molecules (including, but not limited to, nutraceuticals and industrial polymers and polymer subunits), as food products and components of food products, and as biofuel or components of biofuel. Further wherein the pH of the algae slurry is manipulated to allow for automated removal of algae adhered to the light permeable surfaces of the bioreactor.

9 Claims, 9 Drawing Sheets

METHOD OF REMOVING ALGAE ADHERED INSIDE A BIOREACTOR THROUGH COMBINED BACKWASHING AND LOWERING OF PH LEVEL

CROSS-REFERENCE TO RELATED APPLICATIONS

This United States Utility Patent Application claims priority to U.S. Patent Application No. 61/248,398, filed Oct. 2, 2009, which application is hereby incorporated herein by reference in its entirety.

BACKGROUND OF INVENTION

1. Field of the Invention

The present disclosure relates generally to a system and method for the efficient cultivation of algae in systems using in part or in full bioreactor chambers and other units wherein algae are grown in the presence of light and are then harvested for various uses including, but not limited to, for producing specific molecules, including recombinant molecules and other molecules produced from algae especially adapted to produce such molecules (including, but not limited to, nutracenticals and industrial polymers and polymer subunits), as food products and components of food products, and as biofuel or components of biofuel. Further wherein the pH of the algae slurry is manipulated to allow for automated removal of algae adhered to the light permeable surfaces of the bioreactor.

2. Background Art

Due to forces such as climate change, the instability of petroleum prices, and technological advancements, biofuels are being considered as a viable energy alternative. Biofuels made from food sources have proven controversial due to the fluctuating costs of feedstock, the adverse environmental impact presented by those feedstocks, and their effect on food prices and world hunger. It has become clear, therefore, that biofuels made from food crops will not provide the solution to the world's fuel or power generation challenges.

Research and development activities conducted on behalf of government and private industry have resulted in methods to generate biofuels from microscopic algae and similar and/or related microorganisms, which is particularly rich in oils that can be converted into biofuel. Microscopic algae have a yield per acre that is considerably higher than that of any other feedstock and its growth cycles are much shorter than other crops. Further, algae biofuels are biodegradable and are therefore relatively harmless to the environment if spilled.

At the industrial level, bioreactors that use microalgae and/or similar and/or related microorganisms to trap carbon dioxide and mono-nitrogen oxides are in active development in the United States, though the eventual commercial viability of these bioreactors remains in doubt. The success of such ventures will depend on the ability to mass produce algae by maximizing growth cycles and reducing factors that can contribute to the destruction or mutation of the algae in such a way as to diminish its viability or usefulness as a biofuel. Therefore, the development of a bioreactor that is able to efficiently grow and harvest microalgae at a low overall cost is necessary to realize the full potential of biofuels as a viable energy source.

Additionally, algae and/or other similar and/or related microorganisms may be used to produce a number of different products, including but not limited to, specific molecules, including recombinant molecules and other molecules produced from such microorganisms that especially adapted to produce such molecules (including, but not limited to, nutraceuticals and industrial polymers and polymer subunits), as food products, and as components of food products.

However, prior to the present invention, it has been difficult to produce algae in quantities sufficient to meet industrial scale demands. For example, existing technologies for growing algae, for example for use as or in biofuels, can involve "open" or "partially-open" systems wherein algae are grown at least in part in open ponds. However, because light only penetrates to a slight depth in water, such systems produce a low amount of algae per land unit and water volume. There are also problems with evaporation of water, contamination of the algae stock, and unwanted (even potentially dangerous) access of animals (e.g., birds) to the algae as well as other undesirable aspects.

One means to circumvent these problems has been the attempted creation of efficient "closed" or "partially closed" bioreactors. In non-limiting examples, in "closed" bioreactors, an algae and water slurry are typically closed off from access to the outside environment (except, for example, for release of oxygen and other gases created by the growing algae and for the addition of nutrients and other materials to the solution to aid the growth of the algae) for the duration of the growth mode (i.e., prior to harvesting the algae). In "partially closed" bioreactors, part of the growth phase of algae may be in a closed system and part may be in an open system, such as a pond. For example, a closed bioreactor may be used to create a concentrated "seed" slurry of a desired algae which when at a sufficient density is then added to open ponds for further growth prior to harvesting. Such systems may help address issues such as unwanted overgrowth of non-preferred microorganisms in the open ponds due to the high initial seed concentration of the desired microorganism. Advantages of closed over open systems include the ability to potentially control access of the environment to the algae, and vice versa (thereby to, for example, avoid contamination of the algae or unwanted exposure of the algae to the environment and vice versa), to provide tighter controls over optimal conditions for algae growth, to increase the amount of algae produced per land unit and water volume, and to decrease evaporation of water.

Closed bioreactors may contain one or more light permeable "bioreactor" or similar units, regions, or the like, in which algae are exposed to light to induce them to undergo photosynthesis and reproduce. In some such instances, algae slurries may pass through such bioreactors, sometimes repeatedly, thereby maximizing exposure of the algae to light. Also, the algae slurry may be more tightly controlled (than, for example, in a pond of an open system) regarding, for example, nutrient content, pH, and temperature.

However, prior to the present invention, the production of Commercially important amounts of algae using any systems (closed, partially closed, open, and partially open) was limited due to a number of reasons. Some, as discussed, above, relate to open systems. Further, in closed systems problems have been encountered with, for example, algae and other similar microorganisms adhering to surfaces of the units, especially to the light permeable surfaces of bioreactors. This has proven to be a serious problem with the use of closed and partially closed bioreactors to grow algae in commercial quantities. The present invention overcomes these problems enhancing the production of algae and similar and/or related microorganisms for use in commercial applications such as biofuels.

SUMMARY OF INVENTION

In accordance with the invention, algae is cultivated by circulating an algae slurry through a bioreactor that is comprised of a distribution system and a plurality of substantially rigid and translucent bioreactor panels that expose the algae slurry to light. Generally, the system is a low cost automated closed system for growing and harvesting large amounts of algae and other cellular organisms or cells which may subsequently be used in biofuels, and additionally but not limited to in the production of specific products made by algae and other cells including specific lipids and gene expression products. Generally, the system provides for circulating an algae slurry through a closed bioreactor system wherein the algae are exposed to appropriate amounts of light and nutrients, and appropriate waste removal (for example but not limited to oxygen removal) to optimize their growth. The system includes multiple improvements over other systems including being closed, automated, flexible, modular in design, and having improvements overcoming prior limitations in the art such as those caused by algae adhering to the surfaces of such devices, including to light permeable surfaces of bioreactors.

Algae is cultivated by circulating an algae slurry through a bioreactor that is comprised of a distribution system and a plurality of substantially rigid and translucent bioreactor panels that exposes the algae slurry to light. The circulation of the algae slurry through the bioreactor is controlled as a function of process measurements obtained from the bioreactor to maximize the growth of the algae within the bioreactor. Once the algae reaches a predetermined cell density, algae is separated from the algae slurry and the harvested algae can them be further processed and converted into biofuel.

It has been unexpectedly discovered that problems in the prior art involving algae adhering to surfaces of bioreactors, especially to light permeable surfaces of bioreactors, can be overcome by temporarily lowering the pH of the medium in which the algae is suspended. Thus, one may temporarily lower the pH of the solution of algae in a bioreactor for a time sufficient to loosen and/or remove adhered algae (and related microorganisms), which allows the adhered algae to be removed from the surfaces of the system, and then the pH may be returned to the normal or optimal pH for the particular strain of algae. It has further been unexpectedly discovered that this temporary reduction in the pH to levels below that taught in the art (and in fact where the prior teaches not to lower the pH of algae solutions in algae bioreactors as doing so would be harmful to the algae) does not significantly adversely impact the algae and that upon return of the optimum pH the system returns to its prior growth characteristics. Thus, the present invention has discovered a way of overcoming a major obstacle in the prior art which is the problem of algae adhering to surfaces of bioreactors, especially to light permeable surfaces of bioreactors. This is problematic for several reasons, including that it reduces the yield of algae because algae remains adhered in the system, it fouls the surfaces of bioreactors requiring cleaning of the surfaces between uses of the devices and seriously reducing the efficiency of, or even making impossible, continued long-term use of bioreactors without interrupting use to clear the surfaces, and it greatly affects the amount of light that is available to the algae in the light permeable sections of the bioreactors, because algae are known to adhere most to light permeable surfaces, thereby reducing the effectiveness of a bioreactor over time and requiring periodic shutdown and maintenance to either clean or replace surfaces of the bioreactors. Moreover, as discussed below, it has further been unexpectedly discovered that the invention of backwashing of the present invention may be coupled with the invention of lowering the pH of the algae slurry in order to achieve superior backwashing results that can be achieved while the device is operating (i.e., not requiring any shut down maintenance of the device) that allow for the on going, regular cleaning of bioreactor surfaces, including light permeable surfaces, during operation and thus allowing for long term and efficient use of bioreactors.

It has also been unexpectedly discovered that flowing an algae (or a related And/or similar microorganism) through rigid bioreactors wherein the slurry is flowed upwardly, from the bottom to the top of the bioreactor and optionally also through defined serpentine flow-paths in the bioreactor, allows the algae to more readily remain in solution and thus to not settle on and/or adhere to the light permeable surfaces of the bioreactor, including the flow-paths, including serpentine flow-paths, in the bioreactor, as well as providing enhanced fluid flow properties that allow the algae slurry to be passed through the system at flow rates that are determined to maximize and/or optimize flow for optimized exposure of the algae to light while in the bioreactor, yet at the same time, minimize fluid flow disruptions to the cellular integrity of the algae (and other organism).

It has also been unexpectedly discovered that by flowing algae in this manner thorough bioreactors (i.e., flowing the algae upwardly, against the direction of gravity), the system may be readily backwashed by, for non-limiting example, stopping the flow of the algae slurry through the bioreactors, allowing any slurry left in the bioreactors to drain by gravity force into a storage unit, and then reverse the flow of the algae slurry such that it is pumped to move through the bioreactors, including any serpentine channels in the bioreactors, from the top of the bioreactor to the bottom, driven by the force of gravity and/or by additional force provided by a pump, such that the backwashing slurry flows through the bioreactor panels in the direction of gravity and washes off any algae that might have settled on and/or adhered to surfaces of the bioreactor, including surfaces of any serpentine flow-channels, and this algae exits the bottom of the tank into a collection chamber. The system may then be returned to the standard growth mode wherein the algae slurry is moved by, for example, pressure created by a pump (of any kind) to flow upwardly through the bioreactors, to exit as the top of the bioreactors and flow by gravity back to a common collection vessel for repeated recirculation until a desired density of algae is reached at which time (possibly also including a final backwash to collect all algae in the system) the algae is removed from the device for harvesting. As described below, the invention may also be run in a continuous harvest mode wherein amounts of algae are removed from the system as it operates in the recirculation/backwash mode.

Applicants have further unexpectedly discovered that by combining the discovery that reducing the pH of the algae slurry acts to loosen and/or remove algae adhered to surfaces, including light permeable surfaces of bioreactors, with the discovery of the inventive backwashing described herein, provides an unexpectedly superior and synergistic effect when combined. For example, as discussed above and herein, applicants have discovered that a bioreactor system wherein the algae slurry flows against gravity through bioreactor panels in the growth/recirculation phase and wherein the flow may be reversed in order to wash algae from the bioreactor may be combined with the discovery that lowering pH helps loosen and dislodge adhered algae. For example, when the system is operating in a recirculation and/or continuous harvest mode, the pH of the solution may be temporarily lowered (for a non-limiting example, to between about 5.5 and about 7.0, including between about 5.5 and about 6.5, depending on the normal, optimal pH of a particular type of algae as can be readily determined by one of ordinary skill in the art as optimizing variables, including the cleaning (algae releasing)

pH parameters for a particular strain of algae or other microorganism and without undue experimentation), for example by adding additional $CO_2$ gas to the algae slurry as described below, when the desired pH is reached, the system may be changed to the backwash mode. In this manner, the backwashing is done under conditions of the algae medium that are known to loosen and/or remove algae adhered to surfaces of the device, including light permeable surfaces of bioreactor panels. Thus, the combination of the physical force of the fluid flow of the backwash with the loosened or unattached algae caused by the lowered pH creates a synergistic effect in cleaning the surfaces of the device, including the light permeable surfaces of the bioreactor panels, thereby allowing for unexpectedly superior cleaning during the backwash phase. Moreover, as discussed throughout, both the pH reduction and the backwashing may be done while the system is in operating mode (e.g., in recirculation or continuous harvest mode), and thus there is no need to stop the system to clean the surfaces, including the light permeable surfaces of the bioreactors. After a suitable time in the backwash mode to clean the surfaces, the system is changed back to the recirculation and/or continuous harvest mode and the pH of the solution is returned to the optimal pH for the particular strain, for example, by adding pH adjusting agents known in the art to be compatible with the algae. In some embodiments returning the system to the recirculation and/or continuous harvest mode without the need to adjust the pH will reestablish the desired pH, especially when the algae are exposed to sunlight and grow and photosynthesize because the photosynthesis and/or growth consumes the excess $CO_2$ that had been added to the medium in order to lower the pH and, thus, the pH increases until it is in the preferred range for the specific algae for normal operation of the device, and is then controlled by the procedures discussed herein for maintaining optimal pH of the system.

Further, the timing of the backwashing and/or pH reduction may be coordinated with the time at which light is exposed to the system in order to further maximize growth of algae and the effect of lowering pH on removing algae adhered to surfaces within the system. For example, when natural sunlight is used (and/or as supplemented with artificial light) when the intensity of the light is detected by the systems of the inventive device to decrease, this can trigger the $CO_2$ value to open to add $CO_2$ to the system in order to decrease the pH to the desired pH for removing adhered algae. When this pH is reached, pH sensors can under this invention trigger the initiation of the backwashing mode which can operate for a set time and/or, for example, for as long as may be desired to clean the surfaces of the system, including the inner, algae exposed light permeable and/or translucent surfaces of the bioreactor panels. This time varies with the type of algae, the components of the medium, the light intensity, the length of use of the system between complete cleanings, and a host of other factors which can be detected and monitored by an operator. One example is having a light sensor within the flow channels within the bioreactor panels that measures the amount of light energy that reaches the algae in the slurry passing through the panels. The period of time may vary from minutes, to hours, to, for example, overnight. In one embodiment of the invention, the backwashing once triggered as described above, lasts throughout the night until the sunrise at which point the device automatically converts to a recirculation or other mode to allow algae growth and an increase in the pH of the medium.

In an embodiment of the invention, it is important that the lowering of the pH be done while the algae are still exposed to a significant amount of light, for example but not limited to such that the cells are still in photosynthesis and/or growth mode. In some embodiments it has been determined that lowering the pH while the cells are in this light dependent mode further increases the algae releasing effect of lowering the pH of the slurry. In one such embodiment, a light sensor detects when natural daylight is beginning to become reduced, but human or computer operator determines that there is still a sufficient amount of time of sufficient light exposure for the pH to begin and achieve its maximum effect on reducing the adhesion of the algae to the surface of the bioreactor panel surfaces and other surfaces of the system. In such an embodiment, the CO2 value is triggered at the appropriate time to open to add $CO_2$ to the system in order to decrease the pH to the desired pH for removing adhered algae. The lowered pH then acts to help dislodge the adhered algae as described, including but not necessarily requiring, that the device switch to a backwash mode. The time for such removal of adhered algae is then determined as described herein and is generally such that the backwash mode, if selected, operates until a desired amount of adhered algae has been removed from the system. In devices having light sensors within the flow channels of the bioreactor panels, the pH may be lower during periods wherein the device is exposed to natural and/or artificial light and the device may operate until the internal light sensor detects that a sufficient amount of light is reaching the algae in the slurry flowing through the system. This embodiment may include backwashing until, for example, an internal light sensor detects sufficient cleaning of the panel to allow a sufficient amount of light into the system during operation.

In some embodiments, the above described use of internal light sensors may be tied to a source of artificial light. In one such embodiment, the device detects lowering light levels, reduces the pH (for example but not necessarily required, lowering the pH while there is still a sufficient amount of light in the device to optimize the algae removing effect of reducing the pH), for example but not limited to by adding CO2 to the system (which may come, for example, from the flue gas of an industrial plant) and at the desired time, as determined by the procedures described above, switches the system to the backwash mode, a source of artificial light, such as a light bulb of any type, on the outside of a region of a bioreactor panel is turned on (or has been on) and on the inside of the panel near the external location of the light source a light detector detects and determines the increase in the amount of light from the external source to the internal flow algae slurry flow area within the bioreactor panel such that the light sensor determines the amount of algae that is removed in the backwashing (as the backwashing removes algae adhered to the panel near the light source and detector, more light reaches the detector) and when a sufficient amount of light reaches the detector, which level indicates that a sufficient amount of adhered algae has been removed from the wall of the bioreactor to allow the level of light to reach the detector, a manual operator or an automatic device turns off the backwashing mode. At such time, the device may immediately be operated in a recirculation or similar mode if sufficient natural or artificial light is present, or the device may remain paused until sufficient light is available (such as natural light at sunrise) at which point the device is manually or automatically (e.g., as triggered by a sensor of ambient light) to operate in a recirculation or other mode.

In certain embodiments related to any of those described herein, it has been determined, based in part on the type of algae or other organism grown in the system, that is it important to keep the algae at a desired temperature range at all time, including for example, when the device is not in operation (e.g., when it is paused due to a lack of ambient light). In such cases, the aspects of the device responsible for maintaining the temperature of the slurry (for example but not limited to, heat exchanger 121, cooling system 122, expansion tank 124, heater 123, and temperature recirculation pump 125, including associated tubing and the like, operate continuously or intermittently such that the desired temperature range for the specific microorganisms is maintained (the temperature is generally kept between about 20° C. and about 30° C., though the ideal temperature will vary with the particular algae or other microorganism strain)

Once the backwashing is completed (e.g., when the device detects increasing light), the device switches back to the recirculation and/or continuous harvest mode and the pH is either adjusted back to the optimal pH for the particular algae or the pH of the system is allowed to return to a determined pH by the growth and photosynthesis of the algae.

The circulation of the algae slurry through the bioreactor is controlled as a function of process measurements obtained from the bioreactor and includes steps of backwashing, with and without pH reduction, that act to remove algae from light permeable surfaces of bioreactors. Once the algae has reached a sufficient density, the algae slurry is pumped through the harvesting system and then the algae is harvested from the algae slurry. In this way, algae are batch and/or continuously cultivated in a cost effective and efficient manner.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The following U.S. patents and patent applications are incorporated by reference Herein in their entireties:

US Patent Application Publication No. 2009/0029445 (application Ser. No. 11/829,883, filed Jul. 28, 2007) published Jan. 29, 2009;

US Patent Application Publication No. 2009/0081743 (application Ser. No. 11/860,341, filed Sep. 24, 2007) published Mar. 26, 2009;

US Patent Application Publication No. 2007/0289206 (application Ser. No. 11/762,295, filed Jun. 13, 2007) published Dec. 20, 2007;

US Patent Application Publication No. 2009/0011492 (application Ser. No. 11/632,541, filed Jul. 18, 2005) published Jan. 8, 2009;

US Patent Application Publication No. 2008/0178739 (application Ser. No. 11/818,962, filed Jul. 10, 2006) published Jul. 31, 2008;

US Patent Application Publication No. 2008/0118964 (application Ser. No. 10/582,029, filed Jun. 7, 2006) published May 22, 2008;

US Patent Application Publication No. 2008/0009055 (application Ser. No. 11/656,330, filed Jan. 22, 2007) published Jan. 10, 2008;

US Patent Application Publication No. 2005/0239182 (application Ser. No. 11/106,695, filed Apr. 14, 2005) published Oct. 27, 2005;

US Patent Application Publication No. 2005/0260553 (application Ser. No. 10/514,224, filed May 26, 2005) published Nov. 24, 2005;

US Patent Application Publication No. 2005/0064577 (application Ser. No. 10/924,742, filed Aug. 23, 2004) published Mar. 24, 2005;

U.S. Pat. No. 5,541,056 (application Ser. No. 08/279,740, filed Jul. 22, 1994), issued Jul. 30, 1996;

U.S. Pat. No. 5,882,849 (application Ser. No. 08/673,063, filed Jul. 1, 1996), issued Mar. 16, 1999; and U.S. Pat. No. 5,476,787 (application Ser. No. 08/191,457, filed Feb. 3, 1994), issued Dec. 19, 1995.

Other aspects and advantages of the invention will be apparent from the following description and the appended claims.

BRIEF DESCRIPTION OF DRAWINGS

For a more complete understanding of the present invention, reference is Now made to the following descriptions taken in conjunction with the accompanying drawing, in which.

DETAILED DESCRIPTION

Figure 1:
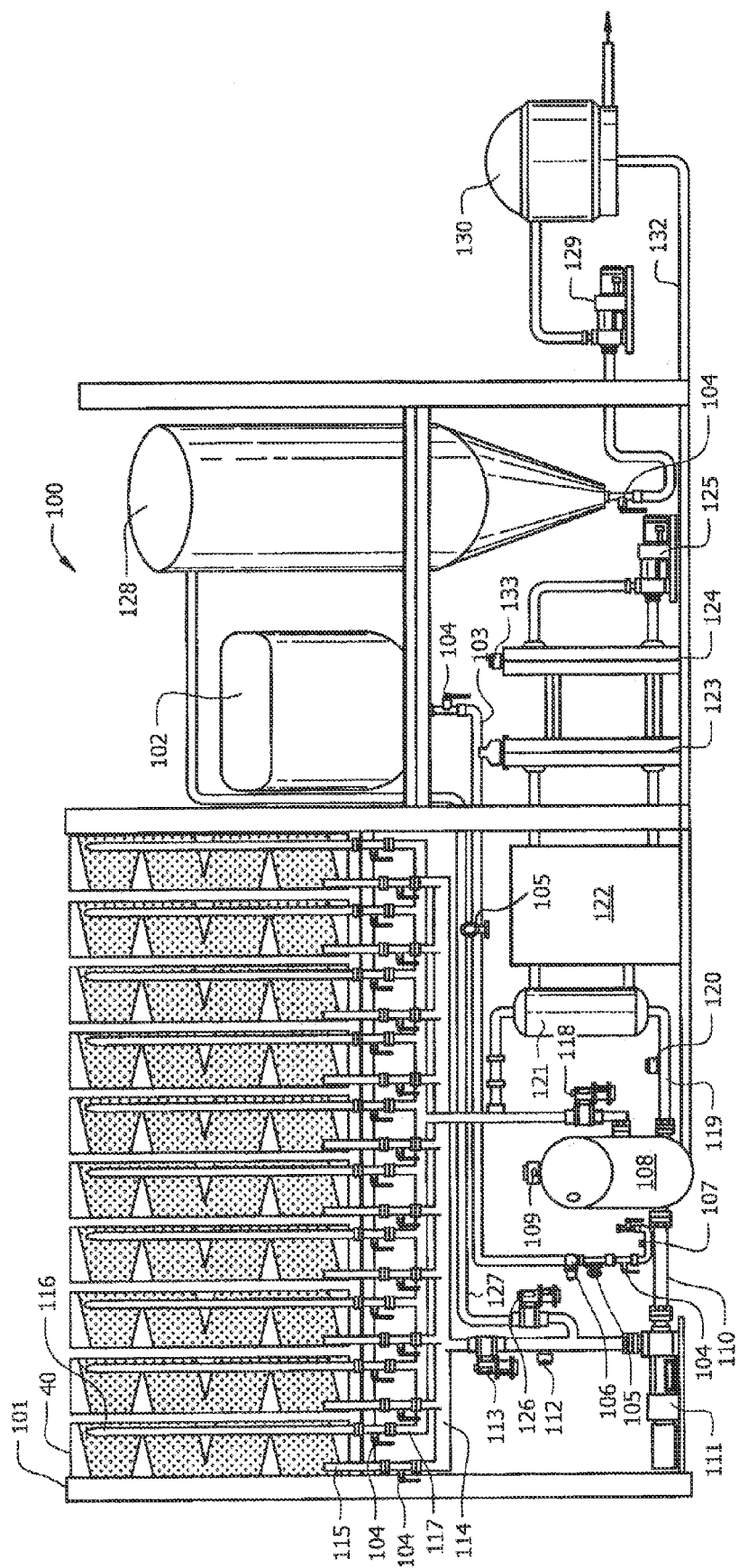
FIG. 1 is a front view of an embodiment of the bioreactor.

FIG. 1 shows an embodiment of bioreactor 100 in which a slurry of nutrients, carbon dioxide, water, and algae are circulated through a distribution system that exposes the slurry to light in order to facilitate the growth and cultivation of microscopic algae. In this embodiment, the components of the substantially self-contained system are mounted onto frame structure 101 that supports the various components in such a way that the entire system is easy to assemble using system components and that facilitates the replacement of independent components should any of the individual components be damaged or otherwise malfunction. Bioreactor panels 40 are mounted side by side in the bioreactor panel rack of frame structure 101 to facilitate quick installation and panel replacement. In the preferred embodiment, bioreactor panels 40 are mounted in an elevated configuration above other components of bioreactor 100. In the embodiment shown in FIG. 1, nutrients needed to promote algae growth, the composition of which may be specially formulated and dependent on the strain of algae sought to be cultivated (e.g., vitamins, nitrates, phosphates, minerals, metals, etc.), are held in nutrient tank 102. Nutrient tank 102 may be made of a variety of materials but is preferably sealed once it has been filled with the necessary nutrients in order to prevent system contamination that could interfere with algae growth. In a preferred embodiment, nutrient tank 102 is substantially impermeable to light to discourage algae from adhering to the surface of the tank. Light impermeability of nutrient tank 102 may be accomplished by any means known in the art, including but not limited to constructing the tank of light impermeable materials, painting or otherwise tinting the tank, covering the tank with light impermeable coating, and/or locating the tank in an area not exposed to light. In the preferred embodiment, nutrient tank 102 is large enough to contain nutrients for multiple batches of algae and is structured so that the nutrients are funneled into raw material piping 103 at the bottom of nutrient tank 102.

Nutrient flow into raw material piping 103 may be regulated, either manually or automatically, by actuating valve 104. In the preferred embodiment, valve 104 is an electronically controlled valve that includes one or more limit switches that send feedback signals via a digital signal, for example, to the process control device to indicate when valve 104 is in the open or closed state. Although the embodiment of FIG. 1 includes valves 104 at various points in the system that may be desirable, other embodiments may include fewer or even no such valves, which may needlessly increase the cost of the system in some cases. In the preferred embodiment, the piping used in bioreactor 100 is primarily polyvinyl chloride (PVC) piping due to its cost effectiveness, durability, and ease of assembly, but the piping may alternatively be comprised of any polymer or metal, and can be flexible or substantially rigid depending, for example, on the environment in which bioreactor 100 will be operating or the characteristics of the strain of algae to be cultivated. In a preferred embodiment, the piping used in bioreactor 100 is substantially impermeable to light to discourage algae from adhering to the surface of the piping. Light impermeability may be accomplished by any means known in the art, including but not limited to constructing the piping of light impermeable materials, painting or otherwise tinting the piping, covering the piping with light impermeable coating, and/or locating the piping in areas not exposed to light. Flow meters 105 and flow transmitters 106 may be incorporated at various points of raw material piping 103 to monitor the rate of nutrient flow in bioreactor 100 and transmit this information to the control system that regulates slurry flow to produce optimum algae growth. Carbon dioxide is injected into the algae slurry at carbon dioxide control valve 107. The flow of carbon dioxide into the system is adjustable based on the requirements of the specific algae strain. Carbon dioxide may be piped from the gas flues of industrial plants to bioreactor 100 through pipes equipped with one or more flow meters and/or analyzers to obtain optimal carbon dioxide flow. As discussed in more detail below, pH altering agents, such as gasses (e.g., $CO_2$), acids and bases, may also be injected or added to the algae slurry, for example at locations such as carbon dioxide control valve 107, at separate such valves, and/or by addition to nutrient tank 102. The addition of pH altering agents into the system is adjustable based on the requirements of the specific algae strain and depending on the phase of the process (e.g., during the backwash phase) as discussed below.

In the present embodiment, the mixing of the nutrients, pH altering agents, and carbon dioxide occurs in close proximity to recirculation tank 108, which contains a mixture of water and lab grown algae that is mixed with the nutrients, pH altering agents, and carbon dioxide as the resulting algae slurry of nutrients, algae, water, and carbon dioxide are pumped through the panel feeder piping 110. In the preferred embodiment, recirculation tank 108 may contain anywhere from 400 to 11,000 gallons of the algae and water mixture, depending on the overall capacity of bioreactor 100. However, the modular design of bioreactor 100 allows for an almost unlimited capacity and therefore the capacity of recirculation tank 108 may be significantly smaller or larger than the capacity of recirculation tank 108 in the preferred embodiment. Depending on the strain of algae sought to be cultivated, various types of water can be mixed with the lab grown algae, such as sweet water, salt water, animal waste, and even waste water that can be supplied from industrial plants, such as coal fired power generation plants or pulp and paper plants. The waste water from such plants may contain at least a portion of the chemicals required to support algae growth, though some initial processing of the waste water may be necessary to remove undesirable components that may be present in the waste water, such as bacteria, for example. Level transmitter 109 sends signals to the control system so that the level of algae and water mixture in recirculation tank 108 can be monitored. Various embodiments of the invention may incorporate level transmitters on any or all tanks and level switches for level verification purposes. In this way, tanks containing water, for example, may be replenished when low tank levels are detected by automatically opening inlet valves and energizing water pumps. Recirculation tank 108 may be made of a variety of materials and is preferably sealed one it has been filled with the necessary nutrients, pH adjusting agents, and carbon dioxide in order to prevent system contamination that could interfere with algae growth. In a preferred embodiment, recirculation tank 108 is substantially impermeable to light to discourage algae from adhering to the surface of the tank. Light impermeability of nutrient tank 102 may be accomplished by any means known in the art, including but not limited to constructing the tank of light impermeable materials, painting or otherwise tinting the tank covering the tank with light impermeable coating, and/or locating the tank in an area not exposed to light.

Recirculation and harvest pump 111 pumps the algae slurry (e.g., water, algae, nutrients, adjusting agents, carbon dioxide) up though bioreactor feeder piping 114, which may incorporate pH probe and transmitter 112 in order for the control system to determine that the pH level of the algae slurry is optimized for algae growth, for example, in the growth mode of the recirculation mode, or is optimized at a reduced pH for the removal of algae adhered to surfaces in the backwash mode of the recirculation mode of the system. The speed of recirculation and harvest pump 111 is controlled using a variable frequency drive that controls the rotational speed of the alternating current (AC) electric motor by varying the frequency of the electrical power supplied to the motor of recirculation and harvest pump 111. Recirculation and harvest pump 111 thereby controls the flow of the algae slurry through bioreactor 100 and operates so that algae wall disruption is limited to keep the algae intact, which promotes the overall growth of the algae. Additionally, recirculation and harvest pump 111 is reversible in flow direction allowing for the backwashing mode of the recirculation mode described herein. As in the growth mode of the recirculation mode, in the backwash mode, the speed of recirculation and harvest pump 111 may be controlled, including by automation, and the pump controls the flow of the algae slurry through bioreactor 100 and operates so that algae cell wall disruption is limited to keep the algae cell walls intact, while maintaining flow sufficient to remove algae adhered to the surfaces of the bioreactor 100, including those of bioreactor panel 40. Several feedback loops, some of which involve recirculation and harvest pump 111, measure and/or control flow totalization, flow rate, system pressure, conductivity, pH level, temperature, and optical density.

The variable frequency drive is part of the control system that utilizes a process control device that compares process measurement variables, such as pH level, algae slurry flow rate, and algae slurry temperature, for example, with predetermined set points that are specifically calculated to produce the optimum growth rate for each strain of algae to be cultivated in the growth mode and, for example, optimum control of lowered pH in the backwash mode of the recirculation mode. Alternative embodiments may use predetermined ranges of set points that may be acceptable depending on the strain of algae being cultivated. It may not be necessary to achieve a particular temperature to the degree if a range of temperatures is adequate to promote algae growth. A process control device may be a Proportional-Integral-Derivative (PID) controller, which is a closed control loop feedback controller that is used to correct an error between a measured process variable and a desired set point (or range of set points) by calculating and outputting a corrective action to adjust the process. The preferred embodiment uses a programmable logic controller (PLC), but other PID-capable controllers, such as mechanical controllers, pneumatic controllers, electronic analog controllers, electronic digital controllers, soft PLCs, or PC-based controllers may also be used. The control system may be located locally, such as in a control panel mounted to an individual bioreactor, or it may be located remotely from the system. The control system may be designed to operate a single bioreactor or many bioreactors.

In a preferred embodiment, the method of device may operate in two modes, a recirculation mode and a harvest mode. Additionally, in a preferred embodiment, the recirculation mode may consist of a growth mode and a backwash mode. In a preferred embodiment, in the growth mode of the recirculation mode, algae slurry proceeds from bioreactor feeder piping 114 and is pumped upward through one of a plurality of bioreactor panels 40. Each bioreactor panel 40 is independently connected to a bioreactor feeder piping inlet 115 through which the algae slurry flows. In the preferred embodiment, bioreactor panels 40 are vertically mounted onto frame structure 101 in an elevated configuration that can accommodate a plurality of bioreactor panels 40 to maximize algae cultivation. Bioreactor panels 40 are interchangeable and easily replaced should panel replacement become necessary. In one embodiment of the invention, bioreactor panel 40 is generally constructed of a material that is light permeable, such as a translucent or transparent material. In one embodiment of the invention, bioreactor panel 40 is generally constructed of a translucent polymer that is substantially rigid to allow for the upward pumping of the algae slurry through bioreactor panel 40 in the growth mode of the growth phase while also exposing the algae slurry to an appropriate amount of light for the photosynthesis reaction necessary for algae growth. By continuously pumping the algae slurry up through bioreactor panel 40 and allowing gravity to carry the algae slurry down through bioreactor piping outlet 116 in the growth mode of the recirculation mode, the amount of algae that settles on the horizontal shelves of bioreactor panel 40 and the amount of algae that sticks to the interior surface of bioreactor panel 40 is minimized so that the overall growth of the algae within bioreactor 100 is maximized and the continuous circulation of the algae slurry through bioreactor 100 is realized. Still further, by continuously pumping the algae slurry up through bioreactor panel 40 in the growth mode of the recirculation mode and allowing the slurry to exit the bioreactor panel 40 only by piping outlet 116, which is located at the top of the bioreactor panel 40, during the growth mode of the recirculation mode, the bioreactor panel 40 is substantially, to completely, filled with the algae slurry such that there is substantially no, or absolutely no, void space within the fluid flow regions of the bioreactor panel 40, such that in the growth mode of the recirculation mode virtually all, or all, of the surface area on the inside of the flow path regions of bioreactor panel 40 is in contact with algae slurry. In a preferred embodiment, in the growth mode of the recirculation mode, any void space (i.e., non-algae slurry solution filled space) within the fluid flow regions bioreactor panel 40 is due only to bubbles that may occasionally form near to top of the flow regions of bioreactor panel 40. Thus, overall, the entirety of the algae slurry flow surface of the bioreactor panel 40 remains substantially to completely in contact with the algae slurry during the growth mode of the recirculation mode.

The preferred embodiment of bioreactor panel 40 is constructed using polyethylene, but any polymer with the appropriate light permeable properties (such as being translucent or transparent to light) appropriate for algae growth and sufficient rigidity to allow for the uninterrupted upward flow of algae slurry through bioreactor panel 40 may be used. The polyethylene used in the preferred embodiment may be high density polyethylene, low density polyethylene, high molecular weight polyethylene, low molecular weight polyethylene, cross-linked polyethylene, or any other variation of polyethylene. The light permeable properties (e.g., the translucent properties) of polyethylene allow for a sufficient amount of light into bioreactor panel 40, while not letting too much light into the system. While not intending to be limiting, it is understood that too much light entering the system could hinder algae growth, as might be the case if the panels were constructed of a more transparent material. While sunlight is the likely source of light for the system, it is expressly anticipated that artificial light sources may be used to facilitate algae growth, either alternatively or in combination with natural sunlight. In some embodiments, artificial light sources will allow the bioreactor to operate completely indoors with little or no exposure to sunlight. Alternative embodiments include additional light sources (e.g., fluorescent, HID, etc.) placed between bioreactor panels 40 to provide additional light for photosynthesis.

In a preferred embodiment, substantially only, or only, bioreactor panel 40 is permeable to light and most, or all, other regions through which the algae slurry flows (e.g., in the recirculation mode) are substantially, or totally, impermeable to light. It is understood at the time of this invention that algae in the algae slurry tend to adhere to surfaces that are permeable to light. Therefore, to reduce algae adhering to algae slurry flow surfaces of the present invention, most, or all, such surfaces that do not have to be permeable to light are not permeable to light. Thus, in a preferred embodiment, only the algae slurry flow pathway surfaces of the bioreactor panel 40 are permeable to light, as these must be in order to allow the algae to grow based on photosynthesis. Most, or all, other algae flow surfaces are substantially, or totally, impermeable to light by any means known in the art, including for example being made of light impermeable materials, painted or otherwise tinted, covered with light impermeable coatings, and/or located in areas not exposed to light.

In a preferred embodiment, in the growth mode of the recirculation mode, the algae slurry is pumped from the bottom of bioreactor panel 40 through the serpentine curves comprising the panel channel up to the top of bioreactor panel 40, at which point the algae slurry exits bioreactor panel 40 through bioreactor piping outlet 116. In some embodiments of the invention, valves 104, which may be manually operated or automated (e.g., electronically controlled), are installed at various connection points throughout bioreactor 100, such as valves 104 shown in FIG. 1 located near bioreactor feeder piping inlet 115 and also near bioreactor piping outlet 116. Such valves may be closed, for example, to facilitate the replacement of individual bioreactor panels while not otherwise disturbing the recirculation or harvesting modes of the bioreactor and allowing the algae slurry to continue to circulate through the remaining bioreactor panels. Bioreactor piping outlet 116 is connected to bioreactor recirculation piping 117, which allows the algae slurry to be recirculated through bioreactor 100 by pumping the algae slurry back through recirculation tank 108 and into panel feeder piping 110. Attached to both bioreactor recirculation piping 117 and recirculation tank 108 is temperature control piping 119 that facilitates the heating or cooling of the algae slurry to maintain an acceptable temperature for the algae growth. Dump valve 118, which can be used to drain system should the need arise, is generally closed during the recirculation phase of the algae cultivation process so that the algae slurry is routed through temperature control piping 119 and through heat exchanger 121 so that the temperature of the algae slurry can be altered if a higher or lower temperature would result in more optimal algae growing conditions.

In the embodiment shown in FIG. 1, temperature transmitter 120 is mounted onto temperature control piping 119 in order for the control system to monitor the temperature of the algae slurry as it circulates through bioreactor 100. Heat exchanger 121 allows for the efficient heat transfer from a temperature control liquid to the algae slurry while preventing the temperature control liquid from coming into direct contact with the algae slurry, thereby preventing potential contamination or unwanted dilution of the algae slurry. Heat exchanger 121 can be counter-flow or parallel flow and the preferred embodiment of the invention uses a shell and tube heat exchanger, though any fluid based heat exchanger may be used. The temperature of the temperature control liquid is adjusted based on its flow through the temperature control system, which in the preferred embodiment is comprised of cooling system 122, immersion heater 123, expansion tank 124, temperature transmitter 133, and temperature circulating pump 125.

Cooling system 122 and immersion heater 123 can be alternatively operated to lower or raise the temperature of the temperature control liquid, which in effect adjusts the temperature of the algae slurry as it is pumped though heat exchanger 121. Temperature transmitter 133 provides the control system with the temperature of the temperature control liquid. Temperature circulating pump 125 pumps the temperature control liquid through the temperature control system and expansion tank 124 prevents temperature circulating pump 125 from cavitating by absorbing excess water pressure and relieving the pressure that might otherwise damage temperature circulating pump 125 or other parts of the temperature control system. In the recirculation mode of the preferred embodiment, the algae slurry circulates through the bioreactor and the temperature of the algae slurry is generally kept between about 20° C. and about 30° C., though the ideal temperature will vary with the particular algae strain. Once the algae is inoculated and introduced into the system, the algae slurry is circulated and recirculated through bioreactor 100 until the algae is ready for harvest.

In the embodiment shown in FIG. 1, once a system operator initiates the recirculation mode of bioreactor 100, for example, by actuating the appropriate toggle located on an operator interface screen that may be located locally or remotely in a separate control facility, recirculation and harvest pump 111 is activated, recirculation valve 113 opens, and the algae slurry is circulated through bioreactor 100, including through bioreactor panels 40. In recirculation mode, the temperature control loop will be a function of a predetermined temperature set point, which will be dependent on the strain of algae sought to be cultivated, compared to the temperature as measured by temperature transmitter 120. Though temperature transmitter is shown in FIG. 1 as located in between heat exchanger 121 and recirculation tank 108, one or more temperature transmitters could be located of various locations in bioreactor 100. For example, temperature transmitter 120 may send a 4-20 mA signal to the process control device (e.g., a PLC) where 4 mA represents 0 degrees Fahrenheit and 20 mA represents 250 degrees Fahrenheit. In the preferred embodiment, nutrients are introduced into the system when the recirculation mode is initiated, for example, when the system operator begins the recirculation mode via the operator interface, and valve 104 opens when a digital signal is sent to the motor of electronically operated valve 104 from the PLC, which receives electrical signals from one or more limit switches incorporated into valve 104 to determine whether valve 104 is in a closed or open state. Nutrients are drawn into raw material piping 103 by the suction applied by recirculation and harvest pump 111. Nutrient tank 102 preferably has a flow transmitter incorporated at the point of nutrient outflow that sends the PLC an analog signal to keep track of the amount of nutrients passing out of nutrient tank 102. Both the composition and the amount of nutrients to be introduced into the system are predetermined and dependent on the strain of algae to be cultivated. Such a flow transmitter may provide to the PLC, for example, a 4-20 mA signal to indicate flow rate and a square wave pulse to indicate totalized flow.

When the bioreactor is operating in recirculation mode, a photocell, which may be locally or remotely mounted, provides a digital signal to the process control device to indicate, for example, when it is daylight or when one or more artificial light sources have been activated. In this embodiment, when the process control device determines that light is sufficient for algae photosynthesis and the pH level is at the appropriate level (e.g., about pH 8.40 or higher), then carbon dioxide control valve 107 opens and the carbon dioxide flows through carbon dioxide control valve 107, which also preferably incorporates a flow transmitter that provides the appropriate feedback signal to the PLC. One skilled in the art will recognize this exemplary PID loop as incorporating three input signals (i.e., photocell, pH level, flow) and one output (i.e., open or close signal to carbon dioxide control valve 107). In the preferred embodiment, carbon dioxide control valve 107 can be incrementally closed or opened based on whether the process control device sends an analog signal of 4 mA (e.g., closed), 20 mA (e.g., open), or somewhere in between to place carbon dioxide control valve in an intermediate state between completely open and completely closed. Certain embodiments of the invention may conserve energy by only circulating the algae slurry during daylight hours when the photosynthesis reaction of the algae is maximized. Other embodiments continuously circulate the algae slurry through bioreactor 100, with or without the presence of artificial light sources that can maximize algae growth in the absence of daylight.

As aspect of the present invention is the unexpected and unpredictable discovery that lowering the pH of the algae slurry results in loosening and/or removing and/or aiding in the removal of algae that have adhered to the inner surfaces of the algae slurry flow paths of the bioreactor 100, especially to the light permeable surfaces of the bioreactor panels 40.

It is known in the art that algae adhere to surfaces in algae bioreactors, especially to light permeable surfaces of bioreactors. In fact, this is known in the art as a major limitation to the use of closed systems using light permeable bioreactors for growing algae, especially on a large commercial scale. The present invention has discovered multiple ways in which this major problem in the art can be overcome: intermittently reversing the flow of the algae slurry to effect backwashing of the bioreactor panel 40 during the recirculation mode, reversing the flow of the algae slurry in the bioreactor 40 during the harvest mode, and lowering the pH of the algae slurry, temporarily during any mode and/or coordinated with the backwashing or harvest modes. Thus, as explained in detail below, this discovery pertains to multiple ways by which algae adhered to the surface of a bioreactor, including to the light permeable surfaces of a bioreactor, can be removed, each of which was heretofore unknown and the results of which are highly unexpected and desirable in the art.

Backwashing is accomplished by intermittently reversing the flow of the algae slurry through the bioreactor panel 40 during the recirculation mode. It is believed to work by physically washing adhered algae from the surfaces of the light permeable bioreactor panels 40. As shown in detail in FIGS. 4-6 and discussed below, bioreactor panel 40 is specifically designed such that its light permeable surfaces that come into contact with the algae slurry during operation (and to which surfaces algae tend to adhere) are especially susceptible to washing fluid forces in the backwash mode, and thus to having adhered algae loosened and removed from its surfaces. In embodiments of the present invention, the backwashing may be done alone or m coordination with lowering the pH of the algae slurry (as discussed in detail below).

The recirculation mode of bioreactor 100 is in recirculation mode is designed to prevent algae from settling on the horizontal shelves of bioreactor panel 40. Nonetheless, some algae may accumulate on the interior surfaces of bioreactor panels 40, which can compromise the overall growth rate realized in the algae slurry. In order to prevent or limit the algae accumulation, bioreactor 100 may employ a backwash mode that removes algae from interior surfaces of bioreactor panels 40 by reversing the flow of the algae slurry through the system. In one embodiment of the invention, once the photocell signals that there is no longer sufficient light to promote photosynthesis of the algae, the process control device implements a timing delay to ensure the absence of usable light before stopping the recirculation mode and initiating the backwash mode. The backwash mode reverses the flow of the algae slurry within the system so that the algae slurry is pumped through downward from bioreactor piping outlet 116 out through feeder piping inlet 115. This flow reversal removes a significant portion of the algae that may have settled on the horizontal shelves of bioreactor panel 40 and flushes the algae into recirculation tank 108. In one embodiment, the backwash mode continues for a predetermined period of time (e.g., one hour), after which time it will revert back to the previous mode (e.g., stopped until photocell indicates presence of daylight, recirculation mode, etc.). The serpentine design of the flow path of the algae solution through bioreactor panel 40, shown in detail in FIGS. 4-6 and discussed in detail below, is specifically designed so that the fluid flow in the backwash mode is especially abrasive on the inner surface of the algae slurry pathway of the bioreactor panel 40, so that the backwashing effectively removes algae that has adhered to the surface.

Still further, as discussed below, in the batch harvest mode of the present invention, the flow of the algae slurry through bioreactor panels 40 is also reversed in the same manner in which it is reversed in the above-described backwash mode. Thus, when the system is operated in the batch harvest mode, algae adhered to the light permeable surfaces of the bioreactor panels 40 are similarly loosened and removed from the surfaces. As with backwashing and as discussed below, the batch harvest mode may be done with or without also lowering the pH of the algae slurry.

Further still, it has been discovered that—unexpectedly and unpredictably—while the optimal operating pH of the algae slurry for the bioreactor 100 is the same as that known in the art for a specific strain of algae being grown (and this is well known and readily determinable by one of ordinary skill in the relevant art), and is generally known to be about pH 8.40 or greater, lowering the pH of the algae slurry loosens the adherence of, and removes, algae adhered to surfaces of bioreactor 100, including the light permeable surfaces of bioreactor panels 40. Thus, it has been unexpectedly discovered that effective removal of algae adhered to surfaces of the bioreactor 100, including the light permeable surfaces of bioreactor panels 40, can be attained by lowering the pH of the algae slurry during any mode of operation, and may be coordinated with the backwash and batch harvest modes for removal of adhered algae from the bioreactor 100.

The amount the pH has to be lowered in order to achieve the inventive loosening and removal of adhered algae varies with the strain of algae and is readily determinable by one of ordinary skill in the art. In non-limiting examples, in embodiments of the invention, the amount of decrease in pH necessary to affect the inventive loosening and/or removal of adhered algae in the present invention depends on the optimal pH for the algae being grown in the device. Non-limiting examples include lowering the pH of the slurry by at least about 0.3 from the specific algae's preferred or optimal pH, more preferably by about 1.0, and most preferably by about 1.5 pH value. However one skilled in the art may readily optimize the parameters of the pH for both the growth phase and the adherence removal phase of a given strain of algae or other microorganism.

In certain embodiments the pH is lowered to about 5.0, in other embodiments, to about 6.5, and in other embodiments to about 7.0. In still other embodiments, the pH is lowered as much as possible depending on the way the pH of the slurry is lowered. For example, it is well known to those of skill in the art that the solubility of carbon dioxide in an aqueous solution such as an algae slurry of the invention decreases as the pH decreases. Therefore, when using carbon dioxide to lower the pH of the algae slurry of the invention there is a natural limit below which carbon dioxide is not sufficiently soluble in the slurry to further lower the pH. However, the inventors have found that this limitation on the ability of carbon dioxide gas to lower pH in a slurry of the invention is not of practical significance because in all embodiments tested the addition of carbon dioxide gas (for example, from the flue gas of an industrial plant such as a fossil fuel power plant) to the algae slurries has lowered the pH of the slurry to a level to where optimal removal of adhered algae is possible. This is especially the case where the pH is lowered while the algae slurry is still exposed to light (i.e., where the pH is lowered by the gas when a sufficient amount of light is still reaching the algae in the slurry and the device is still being run (while not absolutely necessary) in a recirculation of similar algae growth phase prior to running the device in, for example, the backwash and/or harvest mode.

It is to be especially noted that an aspect of this invention is the carbon fixation that occurs when a carbon dioxide containing gas, such as that of a waste flue gas at an industrial plant (for example, but not limited to, a coal fired electrical generation plant) is used in the operation of the device, for example to lower the pH for the cleaning phase. In this step, carbon dioxide containing gas dissolves into the slurry medium. The practical effect of this is the lowering of the pH which as described throughout enhances the ability to remove algae that has adhered to surfaces within the device, including light permeable surfaces in the bioreactor panels. However, this dissolving of carbon dioxide gas into the slurry also provides acts as a "carbon sink" in that is removes carbon dioxide that may have otherwise been released to the atmosphere (leading, for example, to the increased release of carbon dioxide in the atmosphere and potentially affecting global climate change). Rather than being released to the atmosphere, the carbon that is dissolved in the algae slurry to lower the pH remains in the slurry when the algae (and/or other microorganisms) being to grow again in a growth phase (such as the recirculation phase) and this carbon is "fixed" in the biomass of the algae.

The amount of time that the pH may be lowered to achieve the inventive loosening and removal of adhered algae varies with the strain of algae and is readily determinable by one of ordinary skill in the art. In non-limiting examples, in embodiments of the invention the amount of time that the pH can or may be lowered in order to achieve the inventive removal of adhered algae and return of algae to normal, "healthy" growth and photosynthesis may be from less than about one minute, more preferably about one minute, still more preferably about 1 hour, and still more preferably about 2 hours, and still more preferably more than about 2 hours. There is not believed to be a necessary time point at which the pH must be returned to normal. Any necessary timing depends of the strain of algae and is readily determined by one of ordinary skill in the art. In some embodiments, the pH may be lowered when the sun sets and the device determines a decrease in light to the system, CO2 may then be added to lower to pH to the desired level for the specific algae being grown, and the backwashing initiated. In such cases, the backwashing may proceed for as long as necessary and without changing the pH from that set for backwashing. In preferred embodiments this backwashing is done until the panels are substantially clean of adhered algae and/or until the sunlight begins to increase the next morning as detected by the system. In some embodiments, even when the backwashing stops before exposure to light begins, the algae solution may remain at the reduced pH until the system is exposed to light and the system is run in the recirculation or continuous harvest mode. In such cases, the pH may be allowed to increase to the desired optimal level for that strain of algae by the growing and photosynthesizing consuming the extra $CO_2$ that had been initially added to reduce the pH. In other embodiments, the pH may be returned to normal or optimal pH as soon as the backwashing is done, for example, by adding agents to the slurry to increase the pH.

Therefore it has been discovered that generally any lowering of the pH of the algae slurry beyond the optimum pH for the algae being grown results in loosening and dislodging of algae adhered in the bioreactor 100, including algae adhered to the inner surfaces (flow-paths) of bioreactor panels 40. Moreover, it has been discovered that while the prior art teaches against changing the pH from the preferred ranges for specific algae (and other microorganisms) in bioreactors and the like because it is taught that doing so will be deleterious to the microorganisms, including adversely affecting their growth and even killing them, it has been unexpectedly discovered that the pH can be lowered temporarily to cause loosening and removal of algae (and other microorganisms) adhered to surfaces in algae growth systems, such as the inner surface of bioreactor panels 40 and then the pH can be returned to the normal range for optimal growth of the algae (or other microorganism) without having significant deleterious effects on the algae or its growth or production of desired products.

Therefore, in one embodiment, $CO_2$ gas is added to the system at carbon dioxide control valve 107 to lower the pH. In different embodiments this may be done when the device is still in the growth phase and the algae in the slurry passing through the panels are exposed to light, such as in the recirculation phase, or near the end of light exposure to the device. When the pH has been lowered by the desired amount (which amount may readily be determined by one skilled in the art by testing for the pH range at which a specific algae strain or other microorganism will be loosened or removed from adherence to the same material and under the same conditions as that of, for example, bioreactor panel 40, and wherein the algae will remain alive and able to promptly return to growth and photosynthesis when the pH of the algae's medium is adjusted to the algae's optimal pH range and disadhered algae are exposed to light) the system may continue to run, for example in recirculation or continuous harvest mode, and the adhered algae will be removed from the walls of the system, including from those of bioreactor panel 40, and returned to the slurry. Carbon dioxide gas may also be added to the system as described above to lower the pH of the algae slurry and when the pH reaches a desired predetermined range for optimum removal or loosening of adhered algae of the type used in the system, the system can be changed to the backwash mode of operation as described herein. In this case, the backwash is performed with an algae slurry at the pH at which the algae is loosened or removed from surfaces. Thus, in this embodiment, there is a combination of physical force from the flow of fluid through the bioreactor panels 40 as described herein for backwashing combined with the fact that due to the pH of the liquid of the algae slurry, the adhered algae lose their adherence to the surfaces of the bioreactor panel 40. In this embodiment, when the backwashing has cleaned the surfaces of the bioreactor panels 40 sufficiently, the system can be returned to normal operation such as recirculation or continuous harvest mode.

Moreover, it has been unexpectedly discovered that the lower pH is not deleterious to the algae when they are "paused" and are not exposed to light. Therefore, once the pH has been lowered and the panels and other surfaces sufficiently cleaned, the algae and slurry may be kept at the same pH until ambient light increases in the morning. Still further, it has been discovered that it is not necessary to use external agents to increase the pH of the slurry. When ambient light increases to the bioreactor panels, the flow of the slurry in, for example, a growth mode such as recirculation, the pH is increased by the growth of the algae as described herein.

Thus, not only is it not generally necessary to take extra steps to increase the pH, but having the algae naturally increase the pH further allows the growing algae to utilize (to "fix" by incorporating the carbon in new biomolecules) the carbon that is in the slurry as introduced in carbon dioxide gas dissolved into the slurry in the earlier step of lowering the pH. This completes one example of an additional environmentally sound aspect of the present invention, fixation of carbon from a carbon dioxide emitting source such as a coal or other fossil fuel driven power plant.

When, in any embodiment, the adhered algae (or other microorganisms) have been sufficiently removed from surfaces of algae growing devices such as those described herein, the pH may be adjusted back to the optimal range of the specific algae or other microorganism or the algae may be exposed to a source of light, for example in an operating mode such as the recirculation mode, and the algae will consume the excess carbon dioxide that had been added to the system in order to lower the pH, thereby increasing the pH of the algae (or other microorganism) slurry to its optimal range, at which time the system's pH monitoring and adjusting system may maintain the optimal pH until the next time the pH is lowered in order to clean the surfaces of the system.

Additionally, in preferred embodiments of the invention the timing of the lowering of the pH for cleaning the surfaces, and the backwash (if the lowered pH is coupled with a backwash), may be coordinated with exposure of light to the algae (or other microorganisms). For example, in preferred embodiments of the present invention the pH of the medium is lowered when the cells are not exposed to light and is increased when they are exposed to light.

In a non-limiting example, there is a photo switch mounted on the outside of the electrical enclosure that houses the PLC (such as the enclosure of FIG. 2, or FIG. 3, number 301), or to any suitable structure and in any suitable position. There is also a pH probe mounted in the pipeline on the discharge of the recirculation and harvest pump 111, such as shown in FIG. 1, which shows recirculation and harvest pump 111 pumping the algae slurry (e.g., water, algae, nutrients, carbon dioxide) up though bioreactor feeder piping 114, which has incorporated therein pH probe and transmitter 112 (such that a 4-20 Ma signal goes to the PLC) in order for the control system to determine that the pH level of the algae slurry (both for lowering it for removing adhered algae and for maintaining optimal pH in growing conditions). When the photo cell senses a decrease in light and/or the absence light (including sunlight, artificial light or combinations of both), the PLC will open the dioxide control valve 107 to lower the pH to the desired preferred pH for removing adhered algae, which may readily be determined by one of ordinary skill in the art for a given strain or algae or other microorganism and is generally between about 5.5 and 6.5, depending on the microorganism (e.g., algae) strain. Once the pH begins to drop and this signal is read from the pH sensor and transmitted to the PLC, the PLC opens the recirculation valve 113, any overflow valve closes, and dump valve 118 opens while harvest valve 126 closes (although, in other embodiments the harvest valve 126 may remain open if it is desired to harvest during backwashing), and the backwash valve is open. The recirculation and harvest pump 111 is then activated to pump the slurry in the opposite direction as in the recirculation mode, which changes the direction of fluid flow through the bioreactor panels 40. This reversed flow adds the slurry from the top of the panels 40 to exit at the bottom o the panels. This reversed flow passes through the channels of the panel 40 and in doing so removes and flushes out of the bottom of the panels 40 algae (or other microorganisms) that have settled in the panels and/or adhered to the surfaces of the panels and have been removed or loosened by the lowered pH of the slurry ("wash") flow.

In another non-limiting example, there is a photo switch mounted on the outside of the electrical enclosure that houses the PLC (such as the enclosure of FIG. 2, or FIG. 3, number 301), or to any suitable structure and in any suitable position. There is also a pH probe mounted in the pipeline on the discharge of the recirculation and harvest pump 111, such as shown in FIG. 1, which shows recirculation and harvest pump 111 pumping the algae shiny (e.g., water, algae, nutrients, carbon dioxide) up though bioreactor feeder piping 114, which has incorporated therein pH probe and transmitter 112 (such that a 4-20 Ma signal goes to the PLC) in order for the control system to determine that the pH level of the algae slurry (both for lowering it for removing adhered algae and for maintaining optimal pH in growing conditions). When the photo cell senses a that ambient light is decreasing and by an algorithm determines that a certain amount of light sufficient to allow algae growth is left in the day, the PLC will open the dioxide control valve 107 to lower the pH to the desired preferred pH for removing adhered algae, which may readily be determined by one of ordinary skill in the art for a given strain or algae or other microorganism and is generally between about 5.5 and 6.5, depending on the microorganism (e.g., algae) strain. Once the pH begins to drop and this signal is read from the pH sensor and transmitted to the PLC, the PLC allows the addition of carbon dioxide to a pH level that has been determined is optimal for the specific algae for causing the algae to lose adhesiveness to the surfaces in the device. The device will remain in growth phase for a predetermined amount of time prior to the PLC switching the device to a backwashing and/or harvesting mode. It has been determined, unexpectedly, that in certain embodiments, lowering the pH yet allowing the algae to continue to grow in the presence of light by allowing the device to remain in a growth mode in the presence of light following lowering the pH, enhances the effect of the lowered pH on the ability of remove adhered algae. In these embodiments, when a predetermined time has been reached for growing the microorganisms in the presence of both low pH and light (which time may be readily determined by one of ordinary skill in the art through routine optimization of the parameter) the PLC or a manual operator opens the recirculation valve 113, any overflow valve closes, and dump valve 118 opens while harvest valve 126 closes (although, in other embodiments the harvest valve 126 may remain open if it is desired to harvest during backwashing), and the backwash valve is open. The recirculation and harvest pump 111 is then activated to pump the slurry in the opposite direction as in the recirculation mode, which changes the direction of fluid flow through the bioreactor panels 40. This reversed flow adds the slurry from the top of the panels 40 to exit at the bottom o the panels. This reversed flow passes through the channels of the panel 40 and in doing so removes and flushes out of the bottom of the panels 40 algae (or other microorganisms) that have settled in the panels and/or adhered to the surfaces of the panels and have been removed or loosened by the lowered pH of the slurry ("wash") flow.

It has further been discovered that in certain embodiments including with certain algae and other microorganisms, the greater the pH is lowered, the greater the loosening and removal of adhered algae, including in the bioreactor panels 40. Accordingly, one skilled in the art can readily determine the desired levels to which the pH of the algae slurry should be reduced to obtain the most effective loosening and removal of adhered algae. It is generally the lowest level that is compatible with the specific algae and its growth state at the time.

For example, when pH is lowered intermittently in any mode in which algae need to be alive, metabolically active, and intact, such as in the recirculation mode, the pH should be lowered to the known (or readily determinable) minimum pH which the algae slurry can be taken and still maintain living and intact algae. This determination may be influenced by factors such as whether the algae are replicating and/or metabolically active at the time of the pH lowering. For example, it may be known in the art or readily ascertainable that the pH can be lowered to a certain value if the algae being grown are currently being exposed to light and are replicating and/or metabolically active, and that they can be exposed to a lower pH if they are not currently being exposed to light and are replicating and/or are metabolically active. When this applies, the pH can be lowered to a desired level depending on whether the algae are being exposed to light in the bioreactor panel 40. This can be automated as discussed for the automatic control of the backwash based on light levels.

Further still, if the bioreactor 100 is being operated in the batch harvest mode and it is not essential that the algae remain alive, the pH can be lowered to a readily known or ascertainable level at which the algae do not necessarily have to remain viable, but at which they retain any necessary properties for harvesting (such as remaining intact if necessary). As with the example above, these pH levels are either known in the art are determining them is well within the skill on one of ordinary skill in the relevant art without need for undue experimentation.

In a preferred embodiment of the invention, the pH of the algae slurry is lowered at approximately the same time the backwash occurs in the recirculation mode. As discussed above, the backwashing mode can be coordinated with times at which the algae are not exposed to light and this can be coordinated with the pH determinations discussed above.

The pH of the system is measured and controlled as indicated in this specification. The pH of the algae slurry may readily be altered (e.g., temporarily lowered then increased) by techniques well known in the art. For example, pH values may be regulated by pH altering agents such as chemicals, which chemicals may be added to the algae slurry in bioreactor 100 as described above. For example, the pH of the algae slurry may be reduced to a desired level to effect removal of adhered algae by adding additional $CO_2$ or an acid such as $HNO_3$. After the reduced pH has achieved its function of removing adhered algae (e.g., after a backwash), the pH of the algae slurry may be increased to the optimal pH for the specific algae by adding a base, such as $NH_4OH$. Further, by selecting nitrogenous acids and bases, pH regulation may simultaneously add nutrients to the medium. Depending on the nutritional requirements of the species being cultured, phosphorylated acids and bases may be used if phosphorous is preferred over nitrogen as the primary limiting nutrient. Further still, one skilled in the art knows that if the nutrient levels in the algae slurry are high, the use of $CO_2$ to lower the pH may be preferred, whereas if nutrient levels are low, the use of acids that provide nutrients (such as $HNO_3$) may be preferred.

Particular embodiments of the invention may implement a batch harvest mode and/or a continuous harvest mode to extract the algae from the system. For example, the batch harvest mode may be automatically initiated once the algae has reached a predetermined cell density and is ready to be collected. When the algae slurry reaches a predefined algae cell density, which can be measured by optical cell density instrumentation or any other method of measuring algae cell density, an optical density transmitter can send the appropriate analog signal (e.g., 12-20 mA) to the PLC indicating that the current batch of algae is ready to be harvested, at which point bioreactor 100 switches from circulation mode to batch harvest mode in order to begin harvesting the algae. A batch of algae is ready to be harvested when the algae has progressed to a predefined density, which may be determined based on the strain of algae being cultivated as well as the system operator's algae growth objectives. When batch harvest mode begins, recirculation valve 113 closes, dump valve 118 opens to allow bioreactor panels 40 to empty, harvest valve 126 opens, all nutrient and carbon dioxide injections are discontinued, and the algae slurry is pumped through harvest piping 127 to clarifier tank 128. The temperature loop that is executing when bioreactor 100 is in recirculation mode is bypassed in batch harvest mode. When in harvest mode, the speed of recirculation and harvest pump 111 may be adjusted to a predetermined harvest speed that efficiently pumps the algae slurry to clarifier tank 128. Other embodiments of the invention do not include a clarifier tank and alternative means for separating algae from the algae slurry (e.g., screens, filters, etc.) may be connected directly to harvest piping 127 in order to harvest the algae.

Alternatively, when an operator initiates continuous harvest mode from recirculation mode, recirculation valve 113 remains open, harvest valve 126 opens, dump valve 118 closes, the speed of recirculation and harvest pump 111 is adjusted (e.g., 25-35 Hz), the temperature loop that is executing when bioreactor 100 is in recirculation mode continues to execute, nutrient and carbon dioxide injections continue, and the algae slurry is pumped to clarifier tank 128. The continuous harvest mode will continue until the operator selects another mode. Once in clarifier tank 128, the algae, winch is the densest and therefore relatively heaviest component of the algae slurry, collects at the bottom of clarifier tank 128 and is then pumped by centrifuge pump 129 to algae moisture separation device 130 that acts to separate water from algae. In some embodiments of the invention, algae moisture separation device 130 may be a centrifuge-based device, a device that merely screens the algae from the accompanying water, or any other device that separates water and moisture from the algae sought to be cultivated.

The excess water from the process then travels back to recirculation tank 108 through water return line 132 to be utilized in the subsequent batch of algae to be cultivated. After the moisture separation process has been completed, the algae will preferably have a moisture content of no more than 80%-85%. The algae can then be transferred to a holding tank, bin, or silo, for example, and perhaps dried even further using flue gas, steam, or other industrial drying process, and then potentially transported to an oil processing plant for further processing. For certain algae strains, the algae may be harvested once a day, after the initial growing cycle, and processed into oil and algae cake that can then be tested for quality assurance purposes. The growth cycle will be dependent upon the particular strain of algae to be cultivated as well as the objectives set by the system operator.

In alternative embodiments of the invention, instead of being pumped into a clarifier tank, recirculation and harvest pump 111 pumps the algae slurry directly through a filter press using a predetermined density based on the threshold density of the algae to be cultivated (e.g., 1 to 5 microns). As the algae slurry is passed though the filter press, the algae builds up on the filter press plates while the rest of the algae slurry is pumped back into recirculation tank 108. In a preferred embodiment, such a filter press would include a pressure transmitter to sense when a predetermined number of algae has been accumulated and send the appropriate signal to the process control device, at which point the process control device sends the appropriate signals to close all valves and inject compressed air onto the plates to dislodge the filtered algae and empty the algae into a bin located below the filter press or onto a conveyor. Once the algae have been dislodged, the compressed air is turned off and the valves are reopened to process more of the algae slurry. In the case of batch harvesting, the process continues in this way until such time that the optical density transmitter senses an algae density below the desired range that indicates that the recirculation mode should be resumed. Once the process control device receives this signal, the recirculation mode is generally resumed to grow the next batch of algae to be cultivated. In the case of continuous harvesting, all algae that is smaller than a predetermined size (e.g., 3 microns) will pass through the filter press plates and back to the recirculation tank through a water return line to be recirculated through the bioreactor. Alternative embodiments of the invention may use clarifiers, decanters, filter presses, filter bags, or any other method for separating algae from the algae slurry, either mechanically or by using gravity, either alone or in combination with other methods or apparatus.

Bioreactor 100 includes a variety of process measurement devices to determine real-time measurements for the flow of the algae slurry, the temperature of the algae slurry, the system pressure, the conductivity, and the pH level of the algae slurry. In the preferred embodiment, devices such as temperature probes, flow meters, pH probes, or other sensors include analog or digital transmitters to provide process data to the process control system. For example, temperature transmitter 120 may send a current signal to an input on the PLC as part of an analog current loop that utilizes a 4-20 mA signal range with 4 mA representing the lowest end of the temperature range and 20 mA representing the highest end of the temperature range. Signals falling in between 4 mA and 20 mA represent intermediate temperatures between the high and low range and provide the PLC with actual system temperature data that it can compare with the predetermined target temperature that corresponds with the temperature most conducive to maximizing the growth of the strain of algae being cultivated within bioreactor 100. Other analog signals that convey temperature range information that are well known in the art, such as 0-20 mA or 0-10 VDC, may also be used. Likewise, the preferred embodiment utilizes flow meters and flow transmitters, either separate or incorporated into a single unit, and pH level probes and pH level transmitters, either separate or incorporated into a single unit, to convey actual process measurements to the process control device, which is a PLC in the preferred embodiment.

In the preferred embodiment, the process control device implements a computer software program, such as a ladder logic program within a PLC, to compare the actual process measurements (e.g., flow rate, temperature, pressure, conductivity, pH level, etc.) with the predetermined optimal process set points that may vary depending on the strain of algae sought to be cultivated. After the program performs PID calculations to determine the appropriate process control response to effectively move a given process variable closer to the predetermined optimal set point, the process control device sends a signal to the appropriate device (e.g., variable frequency drive, cooling system, heating system, etc.) to implement a change to accomplish this objective. Alternative embodiments utilize an acceptable range of set points, as opposed to a single optimal set point, and the process control device takes corrective action with respect to a given process variable if the applicable process measurement falls outside of the acceptable range.

For example, if a flow meter measures the flow of the algae slurry at 40 GPM and transmits that data to the process control device that compares that actual flow rate to a predetermined optimal rate of 25 GPM, for example, the process control device will perform the necessary calculation to determine how best to adjust the pump speed to reach the desired system flow rate. The process control device would then send a signal (e.g., 4-20 mA) to the variable frequency drive that controls recirculation and harvest pump 111, which in turn may decrease the rotational speed of the AC electric motor by varying the frequency of the electrical power supplied to the motor of recirculation and harvest pump 111. Flow transmitters may also be incorporated into the process inputs in the preferred embodiment. For example, strategically placed flow transmitters measure nutrient usage, water usage, carbon dioxide usage, etc. and allow for the detection of pipe blockage, process trending, and flow characteristics for research and development purposes. Similarly, if the pH level is determined to be too basic based on measurements from the pH probe that are transmitted to the process control device, carbon dioxide can be automatically added to the algae slurry.

If the temperature of the algae slurry is deemed too hot (e.g., temperature measurement exceeds the predetermined set point, temperature measurement exceeds the acceptable predetermined temperature range, etc.), the process control device can turn on the cooling device for the period of time necessary to cool the temperature control liquid to a temperature that will have the effect of cooling the algae slurry to the predetermined optimal temperature or temperature range as a result of the algae slurry flowing through temperature control piping 119 and more specifically through heat exchanger 121. The temperature of the water or other temperature control liquid residing in temperature control system (e.g., temperature control piping, cooling system 122, immersion heater 123, expansion tank 124, etc.) is controlled based on a predetermined temperature set by the bioreactor operator to coincide with the temperature determined to maximize growth of a particular strain of algae that is compared to the actual temperature of the algae slurry as transmitted to the process control device by temperature transmitter 120. Immersion heater 123 or cooling system 122 are energized based on the temperature of the algae slurry compared to the temperature control liquid when the process control device sends a digital signal to contacts or contactors that control immersion heater 123 or cooling system 122. Embodiments of the temperature control system can be comprised of various types of heating elements, a cooling tower or geothermal cooling system, one or more temperature transmitters, automated or manual valves, one or more expansion tanks, one or more temperature circulating pumps, and vents.

Pressure transmitters incorporated into the bioreactor in the preferred embodiment provide measurements of the return line pressure so that the speed of recirculation and harvest pump 111 can be adjusted accordingly to reduce or eliminate vacuum buildup on the return line. Similarly, conductivity transmitters used in conjunction with sensors that continuously measure conductivity (e.g., total dissolved solids or gases) can be used to determine the level of nutrients in the algae slurry and the amount, if any, of nutrients to be added to the algae slurry. Other embodiments of the bioreactor include a carbon dioxide gas analyzer to measure the amount of carbon dioxide present in the algae slurry, and thus the amount of carbon dioxide that the algae is consuming. The carbon dioxide gas analyzer quantifies carbon dioxide usage for carbon dioxide sequestration and is used to minimize excessive carbon dioxide use. The carbon dioxide gas analyzer sends an analog signal to the PLC (e.g., 4-20 mA), where 4 mA represents 0% and 20 mA represents 5%, or 50,000 PPM (parts per million).

Figure 2:
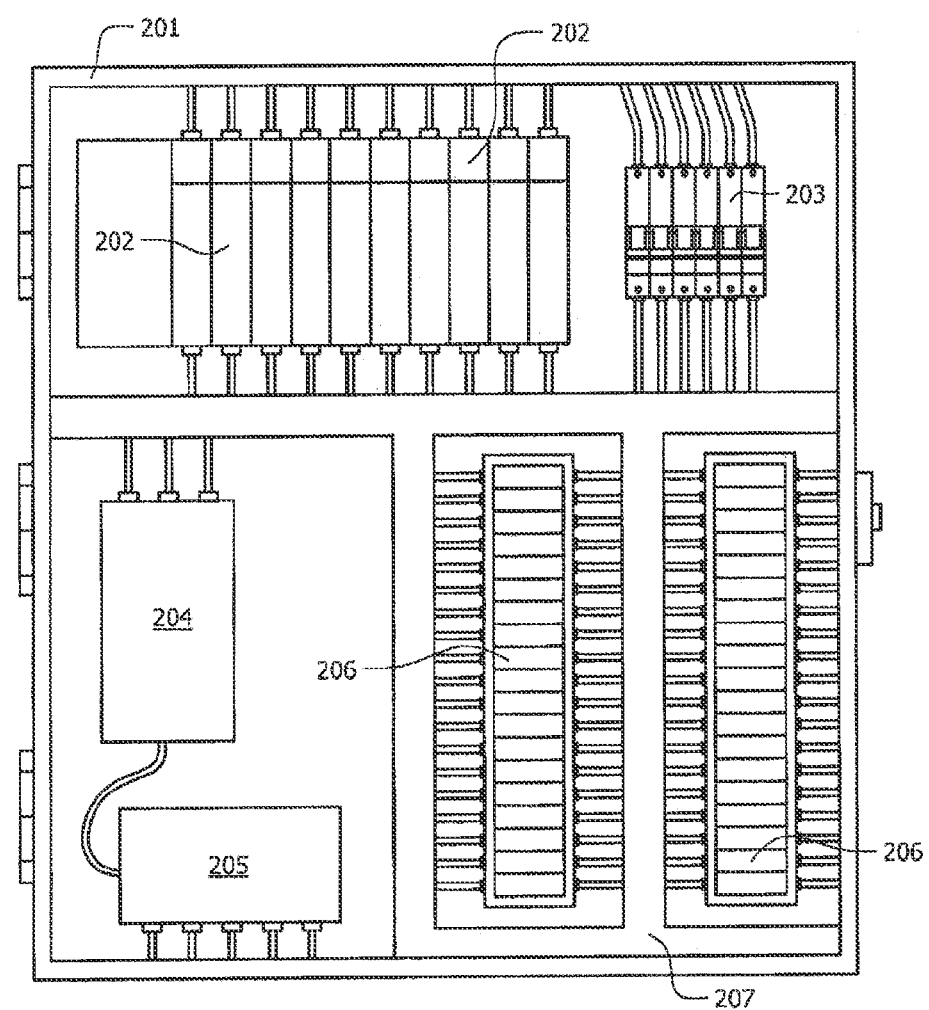
FIG. 2 is a front view of the interior of an embodiment of a control enclosure.
Figure 3:
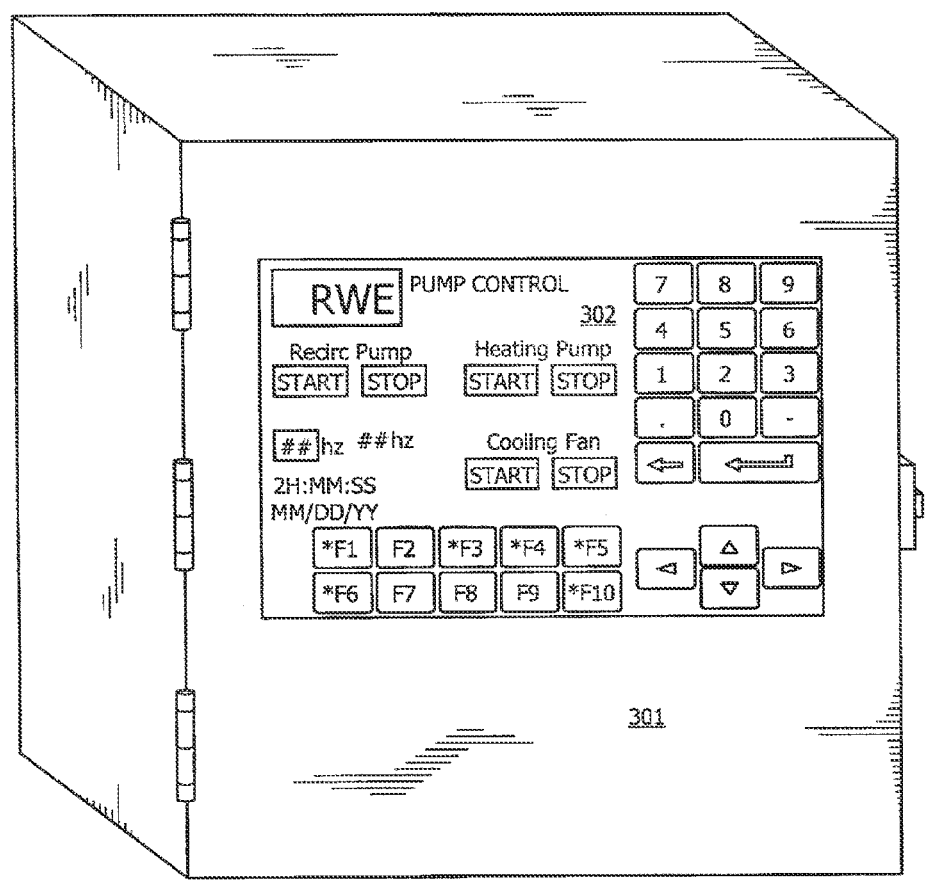
FIG. 3 is a front view of the exterior of an embodiment of a control enclosure.

FIG. 2 is a front view of the interior of an embodiment of a control enclosure that may contain one or more system control components that are mounted onto control panel 201 that is mounted within an enclosure. In this embodiment, the control enclosure houses PLC 202, circuit breakers 203, variable frequency drive 204, power supply 205, panel mounted terminal blocks 206, and wiring duct 207. PLC 202 is a chassis-based, modular PLC that can be used to create a variety of digital and analog input/output modules. In the preferred embodiment, the entire process is a closed loop system and is automated using various process control techniques specially implemented to maximize algae production and collection. An operator interface may provide the system operator with diagnostics and the ability to adjust and/or control the process. Operator interfaces may be connected to PLC 202 using serial communication, DH-485, or any other available protocol (DeviceNet, ControlNet, Ethernet, Remote I/O, etc.) and the interfaces are programmed to receive information from PLC 202 and display process data to the system operator in a useful format. PLC 202 may be programmed to recognize fault conditions in the system by receiving data from the process control sensors, meters, probes, etc. in the bioreactor. For example, if variable frequency drive 204 is in a fault condition or any of the valves are not in the appropriate position, PLC 202 may receive the relevant data in the form of a digital or analog signal and may notify the system operator via the operator interface using a fault signal that may include visual and/or audible components. FIG. 3 is a front view of the exterior of an embodiment of control enclosure 301. Operator interface 302 is mounted to the front of control enclosure 301, which is water resistant in the preferred embodiment and may also have corrosive-resistant properties. Operator interface 302 is also rated (e.g., NEMA 4X) so that the integrity of the enclosure is not compromised by mounting operator interface 302 into the cover of control enclosure 301.

In alternative embodiments, the operator interface may reside on a computer located in the electrical/operator building or may be attached to each bioreactor. For example, in a truly independent embodiment of the invention where a single bioreactor operates independently, a control enclosure containing the process control device and the variable frequency drive, among other control-related components, may have the operator interface panel-mounted onto the enclosure. Regardless of where the operator interface is located, a preferred embodiment of the invention includes an operator interface that allows for the inspection of all process control measurements (e.g., temperature, flow, pH level, carbon dioxide level, pressure, conductivity, etc.) using a visual depiction of the bioreactor operation as determined by the data being obtained from the system by the various meters, sensors, probes, etc. Such a visual assessment of the bioreactor operation provides for an advantageous interface to monitor and/or troubleshoot the bioreactor or a particular batch of algae.

Alternatively, for the production of algae on a larger scale, there may be an electrical/operator building with a PC-based operator interface that is capable of monitoring and controlling multiple bioreactors that can populate entire acres of algae farms. Electrical/operator buildings may contain the electrical equipment to power the algae pumps, instruments, and heating/cooling system, as well as one or more computers and operator interfaces to operate and account for trend/historical information related to temperature, pH level, flow rate, conductivity, pressure, and other control information. In the preferred embodiment, the operator interface allows the operator to select between automatic or manual control of the production process (e.g., open/close valves, turn pumps off and on, perform manual harvests, perform automatic harvests, etc.). Control systems may also be remotely operated and controlled via the Internet using available various commercially available software programs with password protection to ensure that only authorized persons can access the system.

Figure 4:
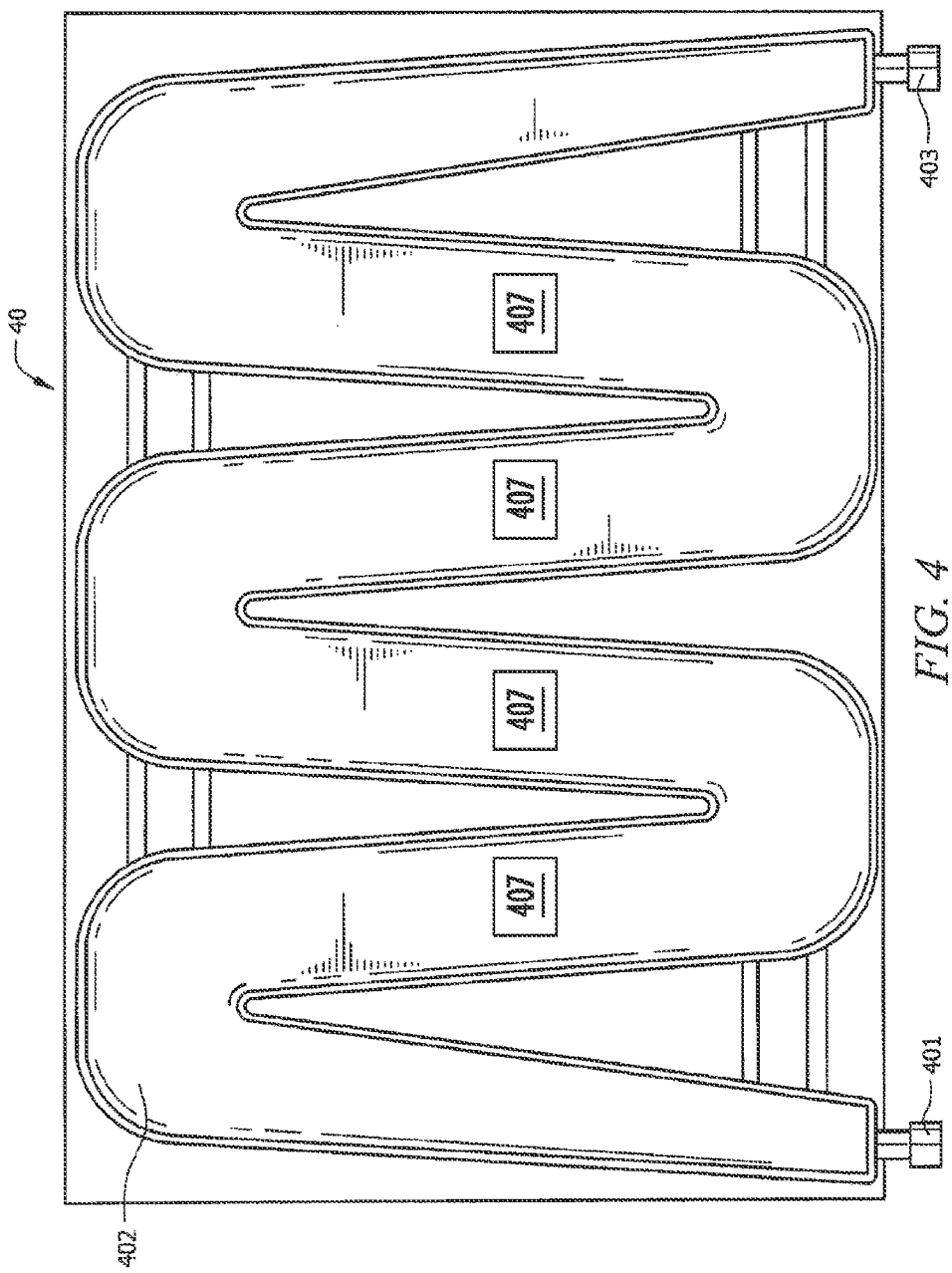
FIG. 4 is a side view of an embodiment of a bioreactor panel.
Figure 5:
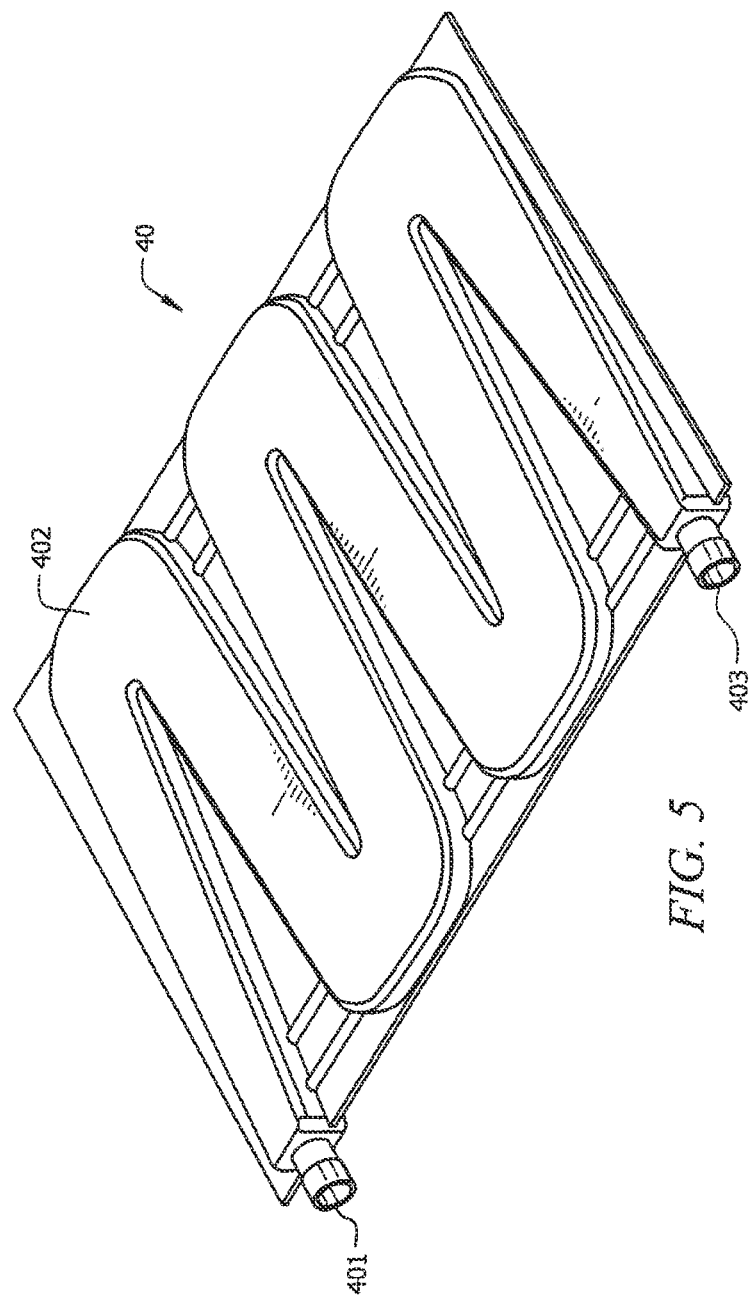
FIG. 5 is an isometric view of an embodiment of a bioreactor panel.

FIG. 4 is a side view of an embodiment of a bioreactor panel. Bioreactor panel 40 is preferably constructed of a rigid translucent polymer such as a low density polyethylene that facilitates the pumping of the algae slurry from panel inlet 401 through flow channel 402 and out through panel outlet 403. Due to the symmetrical nature of this embodiment of bioreactor panel, it is recognized that the orientation of panel onto the bioreactor will determine whether a panel opening is an inlet or an outlet. Since this embodiment of the invention operates such that the algae slurry is pumped from the bottom of bioreactor panel 40 to the top, the opening located at the bottom of bioreactor panel 40 will necessarily be the inlet and the opening located at the top of bioreactor panel 40 will necessarily be the outlet. Bioreactor panel 40, which in one embodiment is approximately 6½ feet high, approximately 4 feet long, and approximately 4 inches wide, is configured to allow the optimum amount of sunlight penetration at a depth of 1.0 inches to 1.5 inches. In the preferred embodiment of the invention, bioreactor panel 40 is made from polyethylene with a smooth interior surface texture that prevents algae from sticking to the interior surfaces of bioreactor panel 40, which in turn keeps the algae slurry circulating through the system to maximize algae growth. The serpentine configuration of flow channel 402 also facilitates the flow of the algae slurry through bioreactor panel 40 at a rate that maximizes the exposure of the algae to light and prevents algae from settling on the horizontal shelves of bioreactor panel 40. FIG. 5 is an isometric view of the embodiment of bioreactor panel 40 shown in FIG. 4.

In FIG. 4, a light intensity sensor 407 is shown. The light intensity sensor 407 (one or more) is positioned to determine if the light inside the loop channels and the flow channels is sufficient to reach the algae slurry and allow the algae to photosynthesize.

Figure 6:
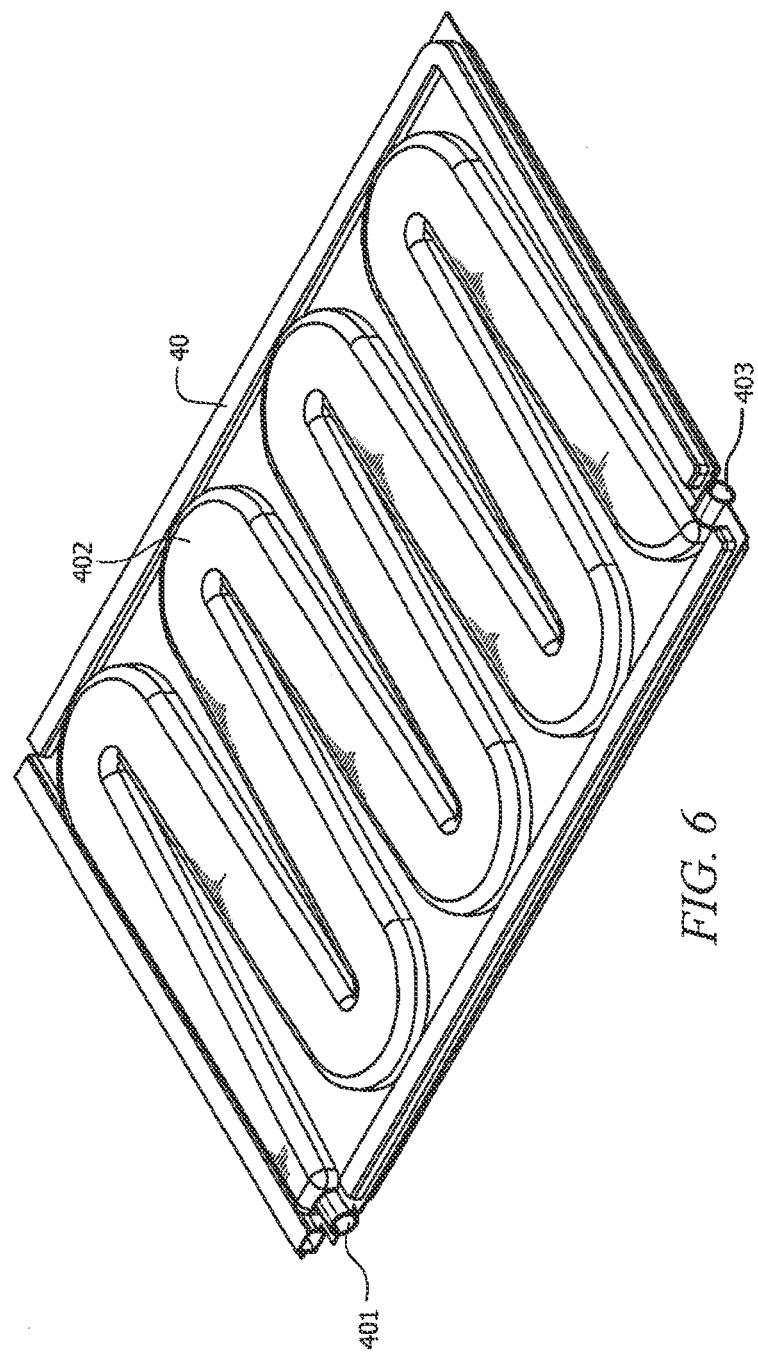
FIG. 6 is an isometric view of an alternative embodiment of a bioreactor.

FIG. 6 is an isometric view of an alternative embodiment of bioreactor panel 40. While the embodiment of bioreactor panel 40 shown in FIG. 4 and FIG. 5 has five independent loops in the flow channel, the embodiment of bioreactor panel 40 shown in FIG. 6 has seven independent loops in flow channel 402. Also, panel inlet 401 is oriented so that the incoming algae slurry enters directly from the side, but exits out the top of bioreactor panel 40 through panel outlet 403. The characteristics of flow channel 402 and its capacity may be altered by changing the diameter of flow channel 402 or by increasing or decreasing the number of independent loops flow channel 402 over the length of bioreactor panel 40. Depending on the embodiment, the exact location of panel inlet 401 and panel outlet 403 may be positioned on the top or side of bioreactor panel 40. While the embodiments of bioreactor panel 40 shown in the figures comprise five and seven independent loops in the channel, other embodiments of the invention may have an even number of loops (e.g., 2, 4, 6, 8, 10, etc.) with the algae slurry exiting from a side of bioreactor panel 40 opposite to that from the side which it entered into bioreactor panel 40 and other embodiments may have an odd number of loops (e.g., 3, 5, 7, 9, 11, etc.).

When implemented via computer-executable instructions, various elements of embodiments of the present invention are in essence the software code defining the operations of such various elements. Examples would include embodiments that use a soft-PLC or other computer-based process control device to monitor and/or control the bioreactor or the use of a PC-based distributed control system that may be used to monitor and/or control a plurality of bioreactors. The executable instructions or software code may be obtained from a readable medium (e.g., a hard drive media, optical media, RAM, EPROM, EEPROM, tape media, cartridge media, flash memory, ROM, memory stick, and/or the like). In fact, readable media can include any medium that can store information.

Figure 7:
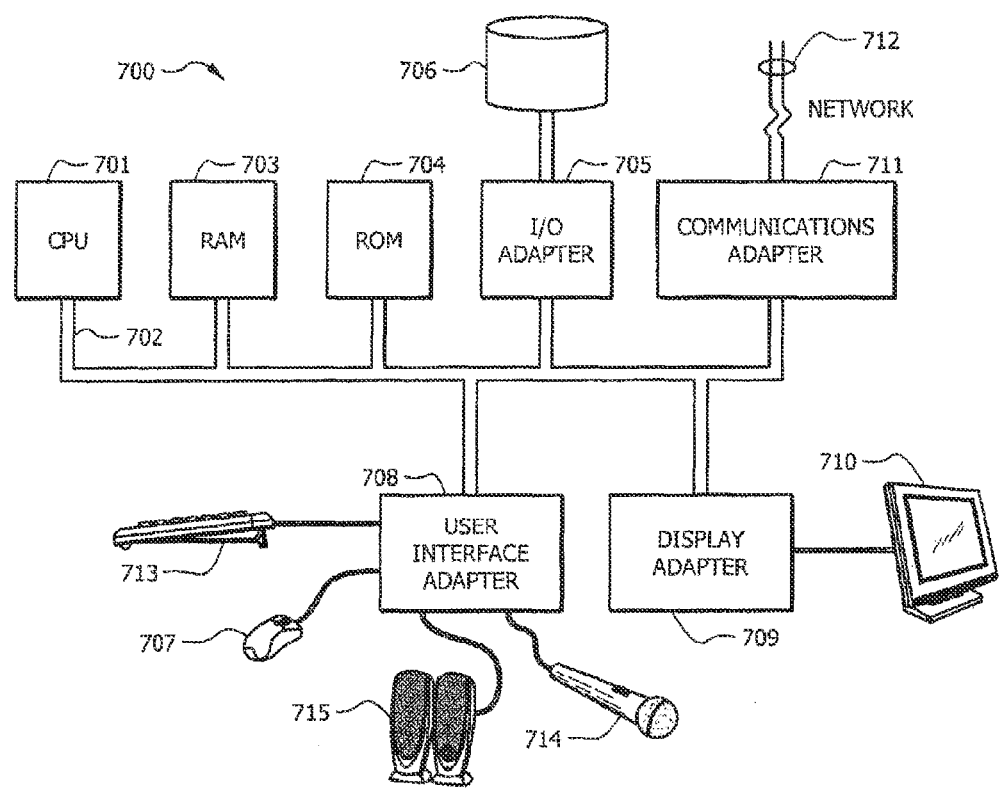
FIG. 7 illustratively represents a computer-based control system adapted according to one embodiment of the invention.

FIG. 7 illustrates an example computer system 700 adapted according to one embodiment of the present invention. That is, computer system 700 comprises an example system on which embodiments of the present invention may be implemented. Central processing unit (CPU) 701 is coupled to system bus 702. CPU 701 may be any general purpose or specialized purpose CPU. However, the present invention is not restricted by the architecture of CPU 701 as long as CPU 701 supports the inventive operations as described herein. CPU 701 may execute the various logical instructions according to embodiments of the present invention. For example, one or more CPUs, such as CPU 701, may execute machine-level instructions according to the exemplary operational flows described above in conjunction with the invention embodiment in which the process control device is a PLC, or to facilitate the remote operation and control of the bioreactor via the Internet, also described above.

Computer system 700 also preferably includes random access memory (RAM) 703, which may be SRAM, DRAM, SDRAM, or the like, and read-only memory (ROM) 704 which may be PROM, EPROM, EEPROM, or the like. RAM 703 and ROM 704 hold user and system data and programs, as is well known in the art. Computer system 700 also preferably includes input/output (110) adapter 705, communications adapter 711, user interface adapter 708, and display adapter 709. 110 adapter 705, user interface adapter 708, and/or communications adapter 711 may, in certain embodiments, enable a user to interact with computer system 700 in order to input information, such as media selections.

I/O adapter 705 preferably connects to storage device(s) 706, such as one or more of hard drive, compact disc (CD) drive, floppy disk drive, tape drive, etc. to computer system 700. The storage devices may be utilized when RAM 703 is insufficient for the memory requirements associated with storing media data. Communications adapter 711 is preferably adapted to couple computer system 700 to network 712 (e.g., the Internet, a LAN, a cellular network, etc.). User interface adapter 708 couples user input devices, such as keyboard 713, pointing device 707, and microphone 714 and/or output devices, such as speaker(s) 715 to computer system 700. Display adapter 709 is driven by CPU 701 to control the display on display device 710 to, for example, display the media as it is played.

While FIG. 7 shows a general-purpose computer, it should be noted that the exact configuration of a portion of a system according to various embodiments may be slightly different. For example, peer devices according to one or more embodiments may be any kind of processor-based device, such as a cell phone, a Personal Digital Assistant, a specialized device (e.g., a stand-alone P2P television module, a home media center that streams television content, Etc.), a set top box (STB-a P2P television module that receives television inputs, such as HDMI and component inputs and outputs to a television or other component), and/or the like. Additionally, servers (e.g., tracker servers) according to one or more embodiments may be any kind of processor-based device capable of sending media streams, such as a personal computer, a server-type computer, a STB, a home media center, and the like. Moreover, embodiments of the present invention may be implemented on application specific integrated circuits (ASICs) or very large scale integrated (VLSI) circuits. In fact, persons of ordinary skill in the art may utilize any number of suitable structures capable of executing logical operations according to the embodiments of the present invention.

Figure 8:
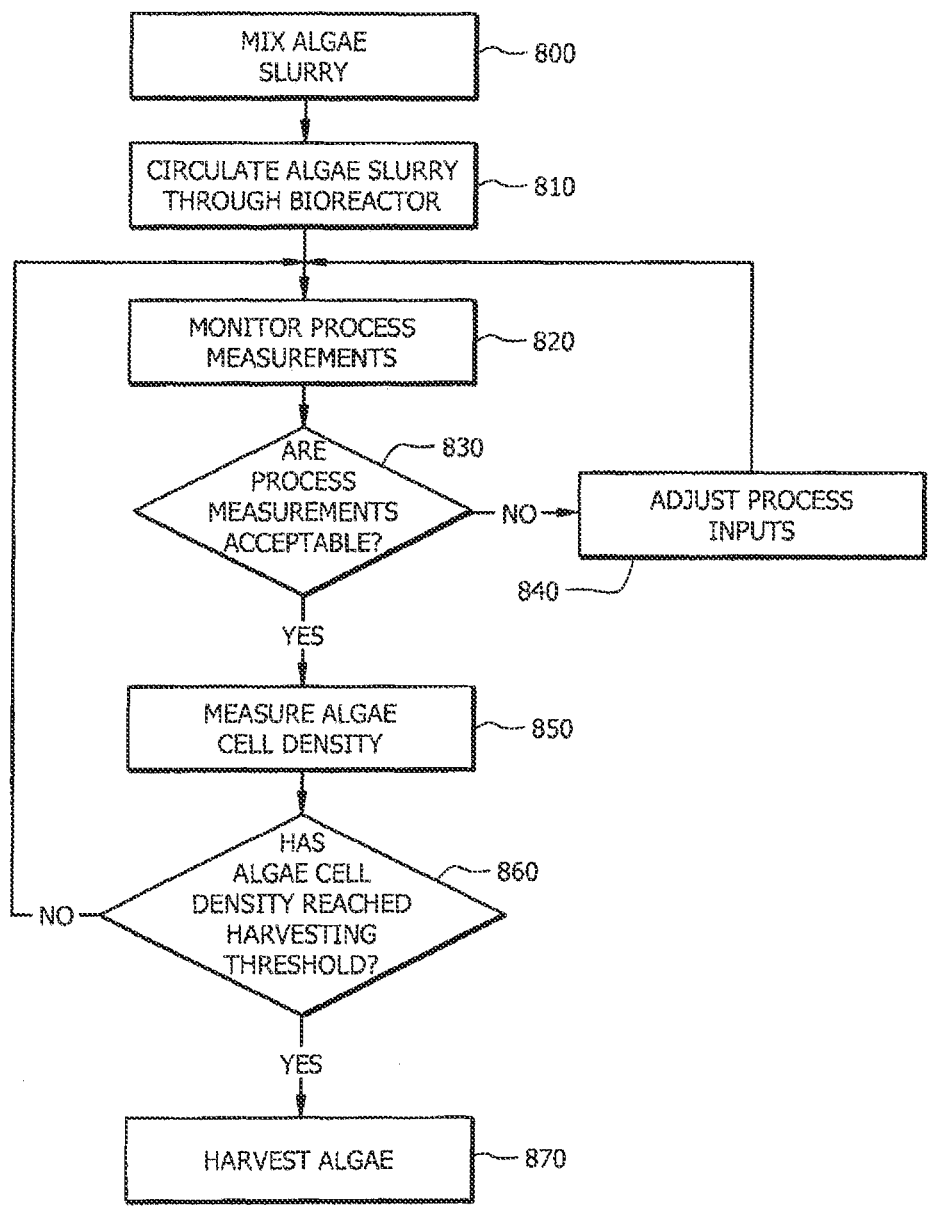
FIG. 8 is a flow chart demonstrating an embodiment of a method for cultivating algae.

FIG. 8 is a flow chart demonstrating an embodiment of a method for cultivating algae. Process 800 mixes the algae slurry together, for example, by mixing algae, water, nutrients, and carbon dioxide together. Process 810 then circulates the algae slurry through a bioreactor. Process 820 monitors various process measurements obtained from the bioreactor (e.g., flow rate, temperature, pressure, conductivity, pH level, etc.). Decision 830 determines whether all of the applicable process measurements are acceptable (e.g., each process measurement equals the optimal set point for that process variable, each process measurement falls into the acceptable range of set points for that process variable, etc.). If any of the process measurements are not acceptable, process 840 adjusts one or more of the process inputs (e.g., recirculation and harvest pump, cooling system, heating system, etc.) to bring the process measurement or measurements to an acceptable value or into an acceptable range, at which point the method resumes at process 820. If decision 830 determines that all of the applicable process measurements are acceptable, process 850 measures the algae cell density of the algae slurry. Decision 860 determines whether the algae cell density has reached the desired threshold density to begin the harvesting process. If the algae cell density has not reached the desired level to indicate that the algae should be harvested, the method resumes at process 820. If decision 860 determines that the algae cell density has reached the desired level, then process 870 harvests the algae.

Generally, the system is a low cost automated closed system for growing and harvesting large amounts of algae, similar microorganisms, or cells (which may have originally come from multicellular organisms, including plants and/or containing aspects of plant cells), for example, wherein the cells require or can use light in order to replicate or otherwise perform functions. The bioreactor 100 and its use expressly covers the use of genetically engineered cells including cells capable of expressing recombinant proteins or other molecules. It is within the level of ordinary skill in the relevant art to use the present invention to, for example, grow recombinant expression cells and induce expression of the recombinant product(s) (e.g., by the introduction of an expression inducing agent or condition at a determined time in the growth of the cells in the bioreactor 100). Thus, the present invention may be used to obtain cells that may subsequently be used for any purpose, including for food, as biofuels, in chemical and industrial applications including but not limited to polymer production such as in plastics, and in the production of specific products made by the cells, including specific lipids and gene expression products, including but not limited to those made by or involving genetic engineering, including but not limited to genetically engineered molecules such as proteins, nutraceuticals, and pharmaceuticals.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Figure 9:
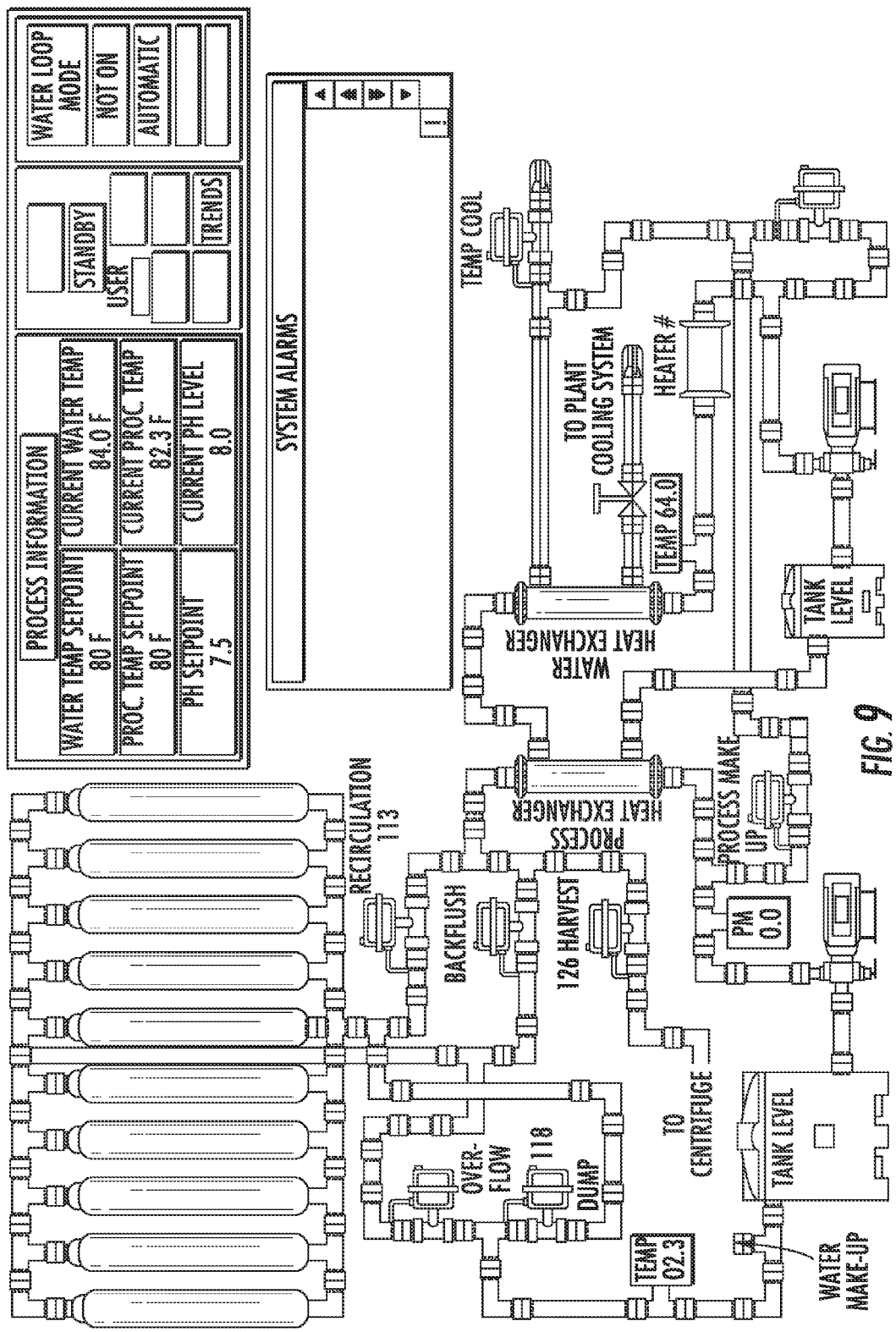
FIG. 9 is a front view of an embodiment of the bioreactor.

FIG. 9 shows another embodiment of a bioreactor of the present invention, including showing, for example but not limited to, dump valve 118, harvest valve 126, and recirculation valve 113.

In still further examples of embodiments of the present invention, the invention includes method for cultivating algae by circulating an algae slurry though a bioreactor, the bioreactor comprising a plurality of substantially rigid and translucent bioreactor panels exposing the algae slurry to light; controlling the circulation as a function of process measurements obtained from the bioreactor; and separating algae from said algae slurry when said algae slurry reaches a predetermined algae cell density.

Other illustrative embodiments include the above described method further wherein: i) the water is saved for use in a subsequent batch of said algae slurry. ii) the process measurements are selected from a list of: actual flow rate, actual pH level, actual conductivity, and actual temperature of said algae slurry and actual pressure level within said bioreactor; iv) the controlling involves comparing the process measurements with predetermined set points and implementing one or more proportional-integral-derivative algorithms wherein the predetermined set points are dependent on a type of algae strain being cultivated; v) the pumping said algae slurry is upward through vertically mounted bioreactor panels which may be done by pumping the algae slurry into panel inlets located at bottom of said bioreactor panels and out of panel outlets located at top of the bioreactor panels; vi) wherein the circulating is constant prior to the separating of the algae from the algae slurry; vii) the algae slurry comprises algae, carbon dioxide, nutrients, and water; viii) the method further includes reversing the circulation of the algae slurry to prevent algae from accumulating on interior surfaces of the bioreactor panels; ix) the method includes temporally reducing the pH of the algae slurry so that algae adhered to inner surfaces of the bioreactor panels or any other inner surfaces are loosened or removed, and may further include lowering the pH by between about 0.3 pH units to about 1 unit, to about 1.5 units and to greater than about 1.5 pH units, and wherein the pH is lowered for a time sufficient to remove adhered algae, also wherein the pH is lowered by adding carbon dioxide to the algae slurry and wherein the pH may be returned to the operating pH by photosynthesis of the algae, which photosynthesis consumes the excess carbon dioxide, and further wherein the lowering of the pH is done when the system is not exposed to light (and the increase of the pH may be done in the presence of light); and wherein the pH is reduced in conjunction with reversing the circulation of the algae slurry to prevent algae from accumulating on interior surfaces of the bioreactor panels.

Still further embodiments of the present invention include, for example, a computer program product having computer program logic recorded on a computer readable medium for cultivating algae, the computer program product including: i) code for controlling a flow rate of an algae slurry through a bioreactor based on one or more flow measurements obtained from the bioreactor; ii) code for controlling a temperature of said algae slurry in said bioreactor based on one or more temperature measurements obtained from said bioreactor; iii) code for controlling a pH level of said algae slurry in said bioreactor based on one or more pH measurements obtained from said bioreactor, including for controlling the pH when the pH is lowered to clean the bioreactor panels by removing adhered algae; and iv) code for determining a completion of algae production cycle based on one or more algae cell density measurements obtained from the bioreactor. Further embodiments include the above computer program further: i) having code for controlling a conductivity of the algae slurry in the bioreactor based on one or more conductivity measurements obtained from the bioreactor; ii) code for controlling a pressure within the bioreactor based on one or more pressure measurements obtained from said bioreactor. iii) code for controlling the separation of algae from the algae slurry; iv) code for controlling the mixing of algae, nutrients, water, and carbon dioxide together to produce the algae slurry; v) wherein the flow rate controlling implements a proportional-integral-derivative algorithm; vi) wherein the temperature controlling code implements a proportional-integral-derivative algorithm; vii) wherein the pH level controlling code implements a proportional-integral-derivative algorithm; and viii) the computer program further having code for controlling the reversal of flow of the algae slurry through the bioreactor and for controlling temporary reduction in the pH for removing adhered algae.

Still further, a specific embodiment of the invention includes a bioreactor to produce algae, the bioreactor having a distribution system for routing an algae slurry flow through the bioreactor, a plurality of substantially rigid and vertically mounted substantially translucent panels for flowing the algae solution and exposing the algae slurry to light, and one or more devices for controlling the algae slurry flow through the bioreactor based on flow rate, temperature, conductivity, and pH level of the algae slurry as measured while the slurry is flowing through the bioreactor.

Still further, in preferred embodiments, the algae slurry may contain algae, nutrients, carbon dioxide, and water. Additionally, in a preferred embodiment, the flow of the algae containing slurry may be controlled by a process control device. Further, in a preferred embodiment of the invention, a process control device controls at least one valve, pump, or variable frequency drive. In a preferred embodiment of the above, the process control device is a programmable logic controller.

In further embodiments of the invention, the bioreactor panels have: inlets located at bottom of the translucent panels and outlets located at top of the translucent panels, and the algae slurry is pumped into the inlets and out of the outlets.

In still additional preferred embodiments, the above described bioreactor further includes a harvesting system for pumping algae slurry out of the distribution system once the algae cell density reaches a predetermined level. In further embodiments, the harvested algae is separated from the algae slurry by, but not limited to, any of a filter press, a centrifuge, or a clarifier tank.

Still further, the invention includes, for example, a method for cultivating algae comprising: mixing algae, nutrients, carbon dioxide, and water to form an algae slurry, pumping said algae slurry through a bioreactor comprising a plurality of translucent panels and a distribution system such that the algae slurry is exposed to light while being pumped upward through one of said plurality of panels during a single circulation cycle, monitoring process measurements obtained from the bioreactor, controlling flow, temperature, and pH level of the algae slurry through said bioreactor as a function of monitored process measurements, and separating algae from the algae slurry when the algae slurry reaches a predefined algae density.

Still further, the invention includes the above method wherein the translucent panels comprise: an integral watertight channel; a panel inlet located at bottom of the translucent panel; and a panel outlet located at top of the translucent panel, and where the translucent panel is substantially rigid and further wherein the integral watertight channel begins at the panel inlet and ends at the panel outlet.

In additional embodiments of the invention, include a translucent thermoplastic bioreactor panel comprising: an integral watertight channel; a panel inlet located at the bottom of said translucent thermoplastic bioreactor panel; and a panel outlet located at the top of said translucent thermoplastic bioreactor panel; and wherein said translucent thermoplastic bioreactor panel is substantially rigid and further wherein said integral watertight channel begins at said panel inlet and ends at said panel outlet.

The invention further includes, for example, the translucent thermoplastic bioreactor panel described above wherein the integral watertight channel has a pathway of serpentine loops internal to the translucent thermoplastic bioreactor panel and further wherein the channel cross-section is smallest at the panel inlet and the panel outlet junctures and is otherwise substantially uniform throughout length of the integral watertight channel.

In further specific embodiments, and solely for purposes of illustration and not limitation, a translucent thermoplastic bioreactor panel may be approximately high, approximately 4' long, and 4" wide, and the panel may have a pathway with three or more independent serpentine loops which are independent curves that span from one side of the panel to the opposite side.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method of algae cultivation including the removal of adhered algae from a bioreactor comprising the steps of:
   (a) circulating an algae slurry through a bioreactor in a first mode;
      wherein the bioreactor comprises a plurality of translucent bioreactor panels, vertically arranged, and a distribution system comprising connecting tubing for flowing the slurry;
      wherein, in the first mode the slurry is pumped in a first flow direction, through the distribution system, into the bioreactor panels through openings in the bottoms, into flow channels located within the panels, upward through the channels, out of the panels through an opening at the top, and back into the distribution system;
   (b) sensing a first light intensity sufficient to penetrate the translucent bioreactor panels using at least one sensor located within the flow channels and sensing a pH level of the slurry;
   (c) maintaining the first mode while the light intensity is at or above the first intensity level, thereby allowing the algae to photosynthesize;
   (d) adding gaseous carbon dioxide to the algae slurry to lower the pH level to a substantially optimum level for algae growth when the sensed pH level has increased above said optimum pH level, due to algae photosynthesis;
   (e) continuing to circulate in the first mode, regulating the optimum pH level, until a second light intensity level is sensed;
      wherein, the second intensity level is below the first intensity level and is insufficient to penetrate the translucent bioreactor panels to reach the algae slurry in order to allow the algae to photosynthesize;
   (f) switching to a second circulation mode, having a flow direction opposite the first mode, upon sensing the second intensity level;
   (g) adding gaseous carbon dioxide to the algae slurry to lower the pH level below the optimum level for algae growth;
   (h) removing algae adhered to the interior surfaces of the bioreactor panels by maintaining the second mode;
      wherein, the lowered pH and physical forces due to backwashing act to remove the adhered algae.

2. The method of claim 1, further comprising the steps:
   measuring the cell density of the algae within the slurry; and
   harvesting the algae from the bioreactor when the algae reaches a predefined density.

3. The method of claim 1, wherein the second circulation mode is stopped after a predetermined amount of time and then the first circulation mode restarts upon the first light intensity being sensed.

4. The method of claim 1, wherein the second circulation mode continues until the first light intensity is sensed and the first circulation mode restarts upon sensing the first light intensity.

5. The method of claim 1, wherein the temperature of the algae solution is maintained within a predetermined temperature range.

6. The method of claim 5, wherein the temperature range is between about 20° C. to about 30° C.

7. The method of claim 1, wherein the pH level of the slurry during the second circulation mode is between about 5.0 and 6.5.

8. The method of claim 1, wherein the pH level of the slurry during the second circulation mode is between about 5.0 and 7.0.

9. The method of claim 3 or 4, wherein the pH level upon restarting the first circulation mode is not increased through external agents.

* * * * *